(12) United States Patent
Au et al.

(10) Patent No.: US 7,217,735 B1
(45) Date of Patent: May 15, 2007

(54) METHODS AND COMPOSITIONS FOR ENHANCING DELIVERY OF THERAPEUTIC AGENTS TO TISSUES

(76) Inventors: Jessie L.-S. Au, 2287 Palmleaf Ct., Columbus, OH (US) 43235; Guillaume Wientjes, 2287 Palmleaf Ct., Columbus, OH (US) 43235

( * ) Notice: Subject to any disclaimer, the term of this patent is extended or adjusted under 35 U.S.C. 154(b) by 0 days.

(21) Appl. No.: 09/547,825

(22) Filed: Apr. 7, 2000

Related U.S. Application Data

(60) Provisional application No. 60/128,674, filed on Apr. 9, 1999.

(51) Int. Cl.
*A61K 31/415* (2006.01)
(52) U.S. Cl. ...................................... 514/456
(58) Field of Classification Search ................ 424/457, 424/233.1
See application file for complete search history.

(56) References Cited

U.S. PATENT DOCUMENTS 5,710,134 A     1/1998 Bosslet et al.

FOREIGN PATENT DOCUMENTS

WO      WO 98/32440      7/1998

OTHER PUBLICATIONS

Zhang, et al., Urology, 1998, 52(5):925-931.*
Nielsen, et al, , 1998, Clin Cancer Res, 4(4):835-46.*
Sharma, et al 1996, Oncol Res 8(7-8):281-6.*
Gan, et al., 1996, Cancer Res, 56:2086-93.*
Nicholson, et al. 1997, Eur J Cancer, 33(8):1291-1298.*
Kerr, 1994, Cancer, 73(8):2013-26.*
Gehl et al (Semin Oncol Dec. 1996;23, 6 Suppl 15: 35-8).*
Hortobagyi et al (Semin Oncol, Feb. 24, 1997, 1 Suppl 3, S4-7.*
Merkle et al (Dec. 1998, Gene Therapy, vol. 5, pp. 1631-1641, abstract only).*
Au JL, et al. "Pharmacodynamics of immediate and delayed effects of paclitaxel: role of slow apoptosis and intracellular drug retention". *Cancer Res.* May 15, 1998;58(10):2141-8.
Baguley BC, et al. "Pharmacokinetic/cytokinetic principles in the chemotherapy of solid tumors". *Clin Exp Pharmacol Physiol.* Nov. 1995;22(11):825-8.
Bhalla K, et al. "Characterization of a human myeloid leukemia cell line highly resistant to taxol." *Leukemia.* Mar. 1994;8(3):465-75.
Chen CT, et al. "Pharmacodynamics of doxorubicin in human prostate tumors." *Clin Cancer* Res. Feb. 1998;4(2):277-82.
Derry WB, et al. "Substoichiometric binding of taxol suppresses microtubule dynamics". *Biochemistry.* Feb. 21, 1995;34(7):2203-11.
Durad RE. "Slow penetration of anthracyclines into spheroids and tumors: a therapeutic advantage?" *Cancer Chemother Pharmacol.* 1990;26(3):198-204.
Erlanson M, et al. "Relations between the penetration, binding and average concentration of cytostatic drugs in human tumour spheroids." Cancer Chemother Pharmacol. 1992;29(5):343-53.
Gan Y, et al. "Pharmacodynamics of taxol in human head and neck tumors". *Cancer Res.* May 1, 1996;56(9):2086-93.
Gold R, et al. "Differentiation between cellular apoptosis and necrosis by the combined use of in situ tailing and nick translation techniques." *Lab Invest.* Aug. 1994;71(2):219-25.
Jain RK. "Delivery of molecular medicine to solid tumors". *Science.* Feb. 23, 1996;271(5252):1079-80.
Jekunen AP, et al. "Synergistic interaction between cisplatin and taxol in human ovarian carcinoma cells in vitro". *Br J Cancer.* Feb. 1994;69(2):299-306.
Jordan MA, et al. "Mechanism of mitotic block and inhibition of cell proliferation by taxol at low concentrations". *Proc Natl Acad Sci U S A.* Oct. 15, 1993;90(20):9552-6.
Jordan MA, et al. "Mitotic block induced in HeLa cells by low concentrations of paclitaxel (Taxol) results in abnormal mitotic exit and apoptotic cell death." *Cancer Res.* Feb. 15, 1996;56(4):816-25.
Kang et al. "A kinetic model for taxol accumulation in human cancer cells: In vivo extrapolation" 1997 *Proc Am Assoc Cancer Res* 38:604.
Kerr JF, et al. "Apoptosis. Its significance in cancer and cancer therapy." *Cancer.* Apr. 15, 1994;73(8):2013-26.
Kleinman H et al. "Role of Membrane and Laminin in Metastases and Tumor Growth:" 1990 *Proc Am Assoc Cancer Res* 31:490-491.
Kuh HJ, et al. "Determinants of paclitaxel penetration and accumulation in human solid tumor." *J Pharmacol Exp Ther.* Aug. 1999;290(2):871-80.
Lesser GJ, et al. "The distribution of systemically administered [3H]-paclitaxel in rats: a quantitative autoradiographic study". *Cancer Chemother Pharmacol.* 1995;37(1-2):173-8.
Lopes NM, et al. "Cell kill kinetics and cell cycle effects of taxol on human and hamster ovarian cell lines". *Cancer Chemother Pharmacol.* 1993;32(3):235-42.
Parness J, et al. "Taxol binds to polymerized tubulin in vitro". *J. Cell Biol.* Nov. 1981;91(2 Pt 1):479-87.
Manfredi JJ, et al. "Taxol binds to cellular microtubules". *J Cell Biol.* Sep. 1982;94(3):688-96.
Markman M. "Intraperitoneal therapy of ovarian cancer." *Semin Oncol.* Jun. 1998;25(3):356-60.

(Continued)

*Primary Examiner*—Misook Yu
(74) *Attorney, Agent, or Firm*—Mueller Smith & Matto

(57) ABSTRACT

The invention, at least in part, is directed to methods for enhancing delivery of therapeutic agents, such as macromolecules and drugs, into the interior of tissues, such as solid tissues or tumors. The method initially uses an apoptosis inducing agent, such as paclitaxel, in doses which create channels within the tissues, and enhance the penetration of therapeutic agents to the interior of the tissue. Current methods of treating tissues are often not effective because the therapeutic agents are not delivered to the interior of the tissue. By using the methods and the compositions of the current invention, therapeutic agents can be delivered to the interior of the tissue.

23 Claims, 5 Drawing Sheets

OTHER PUBLICATIONS

Nativ O, et al. "Anti-neoplastic activity of paclitaxel on experimental superficial bladder cancer: in vivo and in vitro studies". *Int J Cancer.* Jan. 27, 1997;70(3):297-301.

Nicholson KM, et al. "Influence of drug exposure parameters on the activity of paclitaxel in multicellular spheroids." *Eur J Cancer.* Jul. 1997;33(8):1291-8.

Pavelic ZP, et al. "Detection of P-glycoprotein with four monoclonal antibodies in normal and tumor tissues" *Arch Otolaryngol Head Neck Surg.* Jul. 1993;119(7):753-7.

Ringel I, et al. "Taxol is converted to 7-epitaxol, a biologically active isomer, in cell culture medium". *J Pharmacol Exp Ther.* Aug. 1987;242(2):692-8.

Saunders DE, et al. "Paclitaxel-induced apoptosis in MCF-7 breast-cancer cells". Int 3 Cancer. Jan. 17, 1997;70(2):214-20.

Schinkel AH, et al. "Characterization of the human MDR3 P-glycoprotein and its recognition by P-glycoprotein-specific monoclonal antibodies". *Cancer Res.* May 15, 1991;51(10):2625-35.

Smith DC. "Chemotherapy for hormone refractory prostate cancer". *Urol Clin North Am.* May 1999;26(2):323-31.

Song D, et al. "Bladder tissue pharmacokinetics of intravesical taxol". *Cancer Chemother Pharmacol.* 1997;40(4):285-92.

Speicher LA, et al. "P-glycoprotein binding and modulation of the multidrug-resistant phenotype by estramustine". *J. Natl Cancer Inst.* May 4, 1994;86(9):688-94.

Toth K, et al. "New immunohistochemical "sandwich" staining method for mdr1 P-glycoprotein detection with JSB-1 monoclonal antibody in formalin-fixed, paraffin-embedded human tissues". *Am J Pathol.* Feb. 1994;144(2):227-36.

Umezawa, K., (1999), Japanese Pub. No. 11322620, "Transcription factor NF kappa B activation inhibitor—comprises coniferin derivative which acts as an apoptosis activator", (Abstract).

Takashi, H., (1998), Japanese Pub. No. 11269065, "Controlling agent for apoptosis resistance of cancer cells", (Abstract).

Ariyoshi, Y. et al., "Study on chemosensitivity of oral squamous cell carcinomas by histoculture drug response assay." Oral Oncol., 39:701-707 (2003).

Au, J. L.-S., et al., "Histocultures of patient head and neck tumors for pharmacodynamics studies." Pharm. Res., 10:1493-1499 (1993).

Au, J. L.-S., et al., "Pharmacologic effects of Paclitaxel in human bladder tumors." Cancer Chemother.Pharmacol., 41:69-74 (1997).

Au, J. L.-S., et al., "Pharmacodynamics of immediate and delayed effects of Paclitaxel: Role of slow apoptosis and intracellular drug retention." Cancer Res., 58:2141-2148 (1998).

Au, J. L.-S., et al., "Methods to improve efficacy of intravesical mitomycin C: results of a randomized phase III trial." J. Natl. Cancer Inst., 93:597-604 (2001).

Au, J. L.-S., et al., "Determinants of drug delivery and transport to solid tumors." J. Control. Release, 74:31-46 (2001).

Au, J. L.-S., et al., Clinical aspects of drug delivery to tumors. J. Control. Release, 78:81-95, 2002.

Chang, A.Y., et al., "Weekly paclitaxel in advanced non-small cell lung cancer." Semin.Oncol., 28:10-13 (2001).

Chen, C.-T., et al., "Differential time dependency of antiproliferative and apoptotic effects of Taxol in human prostate tumors." Urol.Oncol., 3:11-17 (1997).

Chen, C.-T., et al., "Pharmacodynamics of Doxorubicin in human prostate tumors." Clin. Cancer Res., 4:277-282 (1998).

Chen, C.-T., et al., "Androgen-dependent and -independent human prostate xenograft tumors as models for drug activity evacuation." Cancer Res., 58:2777-2783 (1998).

Di Leo, A., et al., "Paclitaxel activity, dose and schedule: data from phase III trials in metastatic breast cancer." Semin.Oncol., 26:27-32 (1999).

Demoy, M., et al., "Time- and concentration-dependent apoptosis and necrosis induced by free and HPMA copolymer-bound doxorubicin human ovarian carcinoma cells." J.Control Release, 69:185-186 (2000).

Fang, J., et al., "Factors and mechanism of "EPR" effect and the enhanced antitumor effects of macromolecular drugs including SMANCS." Adv.Exp.Med.Biol., 519:29-49 (2003). [Abstract only].

Francis, G.E., et al., "Polyethylene glycol modification: relevance of improved methodology to tumor targeting." J Drug Target, 3:321-340 (1996). [Abstract only].

Furukawa, T et al., "The clinical applications of the histoculture drug response assay." Clin. Cancer Res., 1:305-311 (1995).

Gan, Y., et al., "Pharmacodynamics of Taxol in human head and neck tumors." Cancer Res., 56:2086-2093 (1996).

Gan, Y., et al., "Pharmacodynamics of Doxorubicin in human bladder tumors." Clin.Cancer Res., 2:1275-1283 (1996).

Gan, Y., et al., "Cytostatic and apoptotic effects of Paclitaxel in human breast tumors." Cancer Chemother.Pharmacol., 42:177-182 (1998).

Gan, Y., et al., "Antiproliferative and cytotoxic effects of Geldanamycin,Cytochalasin E, Suramin and Thiaacetazone in human prostate xenograft tumor histocultures." Pharm.Res., 15:1760-1766 (1998).

Gan, Y., et al., "Relationship between paclitaxel activity and pathobiology of human solid tumors." Clin.Cancer Res., 4:2949-2955 (1998).

Hoffman, R.M. "Three-dimensional histoculture: origins and applications in cancer research." Cancer Cells, 3:86-92 (1991).

Inoue, T. et al. "Expression level of thymidylate synthase is a good predictor of chemosensitivity to 5-fluorouracil in colorectal cancer." J Gastroenterol. 40:143-147 (2005).

Jang, S.H., et al., "Determinants of paclitaxel uptake, accumulation and retention in solid tumors." Invest. New Drugs, 19:113-123 (2001).

Jang, S.H., et al., "Enhancement of paclitaxel delivery to solid tumors by apoptosis-inducing pretreatment: effect of treatment schedule." J. Pharmacol. Exp. Ther. 296:1035-1042 (2001).

Jang, S.H. et al., "Drug delivery and transport to solid tumors." Pharm. Res., 20:1337-1350 (2003).

Kircheis, R., et al., "Tumor targeting with surface0shielded ligand-polycation DNA complexes." J. Control Release, 72:165-170 (2001).

Kubota, T., et al., "Potential of the histoculture drug-response assay to contribute to cancer patient survival." Clin. Cancer Res., 1:1537-1543 (1995). [Abstract only].

Langer, et al., "Trastuzumab in the Treatment to Advanced Non-Small-Cell Lung Cancer: Is There a Role? Focus on Eastern Cooperative Oncology Group Study 2598"J. Clin. Oncol., 22:1180-1187 (2004).

Lankelma, J. , "Tissue transport of anti-cancer drugs." Current Pharmaceutical Design, 8:1987-1993 (2002).

Markman, et al., "Weekly paclitaxel in the management of ovarian cancer." Semin.Oncol., 27:37-40 (2000).

Millenbaugh, N.J., et al., "Cytostatic and apoptotic effects of Paclitaxel in human ovarian tumors." Pharm.Res., 15:122-127 (1998).

Miller, M., "Targeted cancer therapies attempt to hit the bull's-eye." Journal of National Cancer Institute News. 92:1878-1879 (2000).

Mosby's Drug Consult, "Paclitaxel", (2005).

Muller, I., et al., "Effect of concentration on the cytotoxic mechanism of Doxorubicin-Apoptosis and oxidative DNA damage." Biochem. Biophys.Res. Commun. 230:254-257 (1997).

Nakamura, J. et al., "Histoculture drug response assay, a possible examination system for predicting the antitumor effect of aromatase inhibitors in patients with breast cancer." Anticancer Res. 18:125-128 (1998).

Neville-Webbe, H.L., et al., "Sequence- and Schedule-dependent enhancement of zoledronic acid induced apoptosis by doxorubicin in breast and prostate cancer cells." Int. J. Cancer 113:364-371 (2005).

Ohie, S., et al., "Cisplatin sensitivity of ovarian cancer in the histoculture drug response assay correlates to clinical response to combination chemotherapy with cisplatin, doxorubicin and cyclophosphamide." Anticancer Res., 20:2049-2054 (2000).

Osmak, M., et al., "Inhibition of apoptosis is the cause of resistance to doxorubicin in human breast adenocarcinoma cells." Neoplasma, 45:223-230 (1998).

Potosky, A.L., et al., "Five-year outcomes after prostatectomy or radiotherapy for prostate cancer: the prostate cancer outcomes study." J. Natl. Cancer Inst., 96:1358-1367 (2004). [Abstract only].

Robbins, K.T., et al., "Sponge-gel-supported histoculture drug-response assay for head and neck cancer. Correlations with clinical response to cisplatin." Arch. Otolaryngol. Head Neck Surg., 120:288-292 (1994). [Abstract only].

Schmittgen, T.D., et al., "Cultured human bladder tumors for pharmacodynamic studies." J. Urol., 145:203-207 (1991).

Schmittgen, T.D., et al., "Pharmacodynamics of mitomycin C in cultured human bladder tumors." Cancer Res., 51:3849-3856 (1991).

Schmittgen, T.D., et al., "Correlation of human bladder tumor histoculture proliferation and sensitivity to mitomycin C with tumor pathobiology." J. Urol., 152:1632-1636 (1994).

Serrano, M.J., et al., "Evaluation of a Gemcitabine-Doxorubicin-Paclitaxel combination schedule through flow cytometry assessment of apoptosis extent induced in human breast cancer cell lines." Jpn.J.Cancer Res., 93:559-566 (2002).

Singh, B., et al. "Prediction of survival in patients with head and neck cancer using the histoculture drug response assay." Head Neck, 24:437-442 (2002).

Song, et al., "Bladder Tissue Phamacokinietics and antitumor effect of intravesical 5-fluoridine." Clin.Cancer Res., 3:901-909 (1997).

Straubinger, R.M., et al., "Antivascular and antitumor activities of liposome-associated drugs." Anticancer Res., 24:397-404 (2004).

Sugarbaker,, P.H., et al., "Update on Chemotherapeutic Agents Utilized for Perioperative Intraperitoneal Chemotherapy" Oncologist, 10:112-122, (2005).

Torchilin, V.P., "Fluorescence microscopy to follow the targeting of liposomes and micelles to cells and their intracellular fate." Adv. Drug Delivery Rev., 57: 95-109 (2005).

Toyota, N., et al., "Therapeutic efficacy and apoptosis and necrosis kinetics of doxorubicin compared with cisplatin, combined with whole-body hyperthermia in a rat mammary adenocarcinoma." Int J. Cancer 76:499-505 (1998).

Weaver, J. et al., "Proliferation indices as molecular pharmacodynamic endpoints in evaluation of anticancer drug effect in human solid tumors." Pharm.Res., 15:1546-1551 (1998).

Weaver, J. et al., "Regional heterogeneity and pharmacodynamics in human solid tumor histoculture." Cancer Chemother. Pharmacol., 44:335-342 (1999).

Wientjes, M.G., et al., "Histocultures of human prostate tissues for pharmacologic evaluation." J. Urol., 153:1299-1302 (1995).

Wientjes, M.G. et al., "Recent developments in antitumor drug delivery." AAPS News Magazine, 6:28-29 (2003).

Yen, W.-C., et al., "Differential effect of Taxol in rat primary and metastatic prostate tumors: site-dependent pharmacodynamics." Pharm.Res., 13: 1305-1312 (1996).

Yen, W.-C., et al., "Pharmacodynamic evaluation of Mitomycin C analog BMS-181174 for potential use in intravesical bladder cancer therapy." Pharm.Res., 14:241-245 (1998).

Yokochi, T. and Robertson K.D., "Doxorubicin inhibits DNMT1, resulting in conditional apoptosis." Mol. Pharmacol., 66:1415-1420 (2004).

Zheng, J.H., et al., Time- and concentration-dependent penetration of doxorubicin in prostate tumors. AAPS PharmSci, 3:E15-2001).

* cited by examiner

METHODS AND COMPOSITIONS FOR ENHANCING DELIVERY OF THERAPEUTIC AGENTS TO TISSUES

RELATED APPLICATIONS

This application claims priority to U.S. Provisional Application Ser. No. 60/128,674, entitled "Method to Enhance Delivery of Therapeutics in Regional Therapy," filed on Apr. 9, 1999, the entire contents of which are hereby incorporated herein by reference.

BACKGROUND

Paclitaxel, one of the most important anticancer drugs developed in the past two decades, is active against multiple types of human solid tumors (Rowinsky E K (1993) *J Natl Cancer Inst Monogr* 15:25–37). Paclitaxel has pleiotropic effects; for example, it enhances tubulin polymerization, promotes microtubule assembly, binds to microtubules, stabilizes microtubule dynamics, induces mitotic block at the metaphase/anaphase transition, and induces apoptosis (Parness J and Horwitz S B (1981) *J Cell Biol* 91:479–487; Manfredi J J et al. (1982) *J Cell Biol.* 94:688–696; Jordan M A, et al. (1993) *Proc Natl Acad Sci USA* 90:9552–9556; Jordan M A et al. (1996) *Cancer Res* 56:816–825; Derry W B et al. (1995) *Biochemistry* 34:2203–2211). The intracellular concentration of paclitaxel is critical for its pharmacological effect; drug resistance in several resistant sublines is correlated with reduced intracellular drug accumulation compared with the sensitive parent cell lines (Lopes N M et al. (1993) *Cancer Chemother Pharmacol* 32:235–242; Bhalla K et al. (1994) *Leukemia* 8: 465–475; Jekunen A P et al. (1994) *Br J Cancer* 69:299–306; Riou J F et al. (1994) *Proc Am Assoc Cancer Res* 35:160; Speicher L A et al. (1994) *J Natl Cancer Inst* 86:688–694).

Doxorubicin is an anticancer drug with a wide spectrum of clinical activities. It has been used clinically to treat leukemias, lymphomas, and solid tumors including breast, lung, prostate, and ovarian cancers and sarcomas (Oesterling et al. (1997) In: Cancer: Principles and Practice of Oncology (Eds, DeVita, V. T., Jr., Hellman, S., and Rosenberg, S. A., 1997); Doroshow, J. H. (1996) In: Cancer Chemotherapy and Biotherapy: Principles and Practice (Eds, Chabner, B. A. and Longo, D. L.)). Doxorubicin is one of the most effective agents against hormone-refractory prostate cancer (Smith, D. C. (1999) Urol. Clin. North Am. 26:323–331). It has been shown that in human prostate tumor histocultures, doxorubicin can induce complete inhibition of tumor cell growth with $IC_{50}$ of 61 nM and complete tumor cell death with $LC_{50}$ of 2.1 µM (Chen et al., (1998) Clin. Cancer Res. 4:277–282, 1998).

Drug delivery to the tumor core is necessary to prevent tumor regrowth (Erlanson M et al. (1992) *Cancer Chemother Pharmacol* 29:343–353; Durand R E (1990) *Cancer Chemother Pharmacol* 26:198–204) and is, therefore, an important determinant of treatment efficacy (Jain R K (1996) *Science* 271:1079–1080). Following a systemic intravenous injection, drug delivery to the tumor core involves three processes, i.e., distribution through vascular space, transport across microvascular wall, and diffusion through interstitial space in tumor tissue (Jain R K (1987) *Cancer Res* 47:3039–3051). When the drug is directly injected into a tumor such as by intratumoral injection or by direct instillation into peritumoral space such as in intravesical therapy of superficial bladder cancer and in the intraperitoneal dialysis of ovarian cancer, drug delivery to the tumor is primarily by diffusion through interstitial space (Nativ O et al. (1997) *Int J Cancer* 70:297–301; Song D et al. (1997) *Cancer Chemother Pharmacol* 40:285–292; Markman M (1998) *Semin Oncol* 25:356–360; Markman M et al. (1995) *Semin Oncol* 22:84–87). Movement of paclitaxel in interstitial space, in spite of its relatively low molecular weight (853 Dalton), is likely to behave as a protein because of its extensive binding to proteins in interstitial fluid (Baguley B C et al. (1995) *Clin Exp Pharmacol Physiol* 22:825–828).

A recent study indicates that drug delivery to a tissue during regional therapy depends on the ability of the drug to penetrate the solid tissue. The study indicates that paclitaxel distribution in multicellular spheroids is limited to the periphery, but the barriers to paclitaxel penetration are not known (Nicholson et al. (1997) *Eur. J. Cancer* 33:1291–1298). Accordingly, approaches to delivering therapeutic agents to tissues that allow for penetration of the drug into the tissue are still needed.

SUMMARY

This invention provides methods, and compositions for use therein, for delivering therapeutic agents to tissues, wherein the methods allow for enhanced penetration of the therapeutic agent into the interior of multilayer tissues, such as solid tissues or tumors. The methods involve use of an apoptosis inducing agent, such as paclitaxel, in doses and for periods of time sufficient to cause apoptosis in the tissue to thereby allow for enhanced penetration of the therapeutic agent into the tissue (e.g., by creating channels within the tissues). Thus, the apoptosis inducing agent is used as a pretreatment before the therapeutic dose of the therapeutic agent is delivered to the tissue, and this pretreatment allows for enhanced penetration of the therapeutic agent into the tissue as compared to when the pretreatment is not used. The apoptosis inducing agent may also have therapeutic activity and thus may also be used as the therapeutic agent (i.e., the same drug may be used as the apoptosis inducing agent and the therapeutic agent). Alternatively, the apoptosis inducing agent may be used to enhance delivery of other types of drugs into tissues (i.e., the apoptosis inducing agent and the therapeutic agent may be different drugs).

Accordingly, in one embodiment, the invention pertains to a method for, delivering a therapeutic agent to tissue of a patient, e.g., a mammal, e.g., a human. The method includes administering an apoptosis inducing agent to the patient, and allowing sufficient time for the apoptosis inducing agent to induce apoptosis in the patient's tissue. The tissue can be, for example, liver, muscle (e.g., cardiac, smooth, or skeletal muscle), neuronal, skin or adipose tissue, or a tumor, such as a brain, breast, ovarian, bladder, prostate, skin, colon, lung, liver, or uterine tumor. The apoptosis agent can be administered systemically, locally, regionally; or any combination thereof, such as both locally and regionally (locoregionally).

In a second embodiment, the invention pertains to a method for delivering a therapeutic agent to a patient's tumor (e.g., a cancerous or benign tumor). The method includes administering a dose of an apoptosis inducing agent to a patient, allowing sufficient time for the apotosis inducing agent to induce apoptosis in the tumor; and delivering a dose of a therapeutic agent to said patient. The tumor may be, for example, a brain, breast, ovarian, bladder, prostate, skin, colon, lung, liver, or uterine tumor. Examples of the apoptosis inducing agent include paclitaxel and doxorubicin.

In yet another embodiment, the invention features a method for delivering a chemotherapeutic agent to a tumor in a patient, for example, a human (e.g., a cancer patient). The method includes administering a dose of an apoptosis inducing agent locally or regionally to a patient, allowing sufficient time for said apoptosis inducing agent to induce apoptosis in the tumor, and delivering a dose of a chemotherapeutic agent to said patient. In a further embodiment, the tumor is a cancerous tumor, e.g., a brain, breast, ovarian, bladder, prostate, colon, lung, liver, or uterine tumor.

The invention also pertains to a composition for delivering a therapeutic agent to a patient. The composition includes a quick release formulation of an apoptosis inducing agent, a slow release formulation of a therapeutic agent, and a pharmaceutically acceptable carrier.

The invention also includes microparticles and nanoparticles comprising therapeutic or apoptosis inducing agents. It also includes methods of treating patients using the microparticles or nanoparticles.

The invention also pertains to a kit for the treatment of tumors. The kit contains an apoptosis inducing agent in a pharmaceutically acceptable carrier, a therapeutic agent in a pharmaceutically acceptable carrier, a container, and directions for using the apoptosis inducing agent and the therapeutic agent for the treatment of tumors.

DETAILED DESCRIPTION OF THE INVENTION

Figure 1:
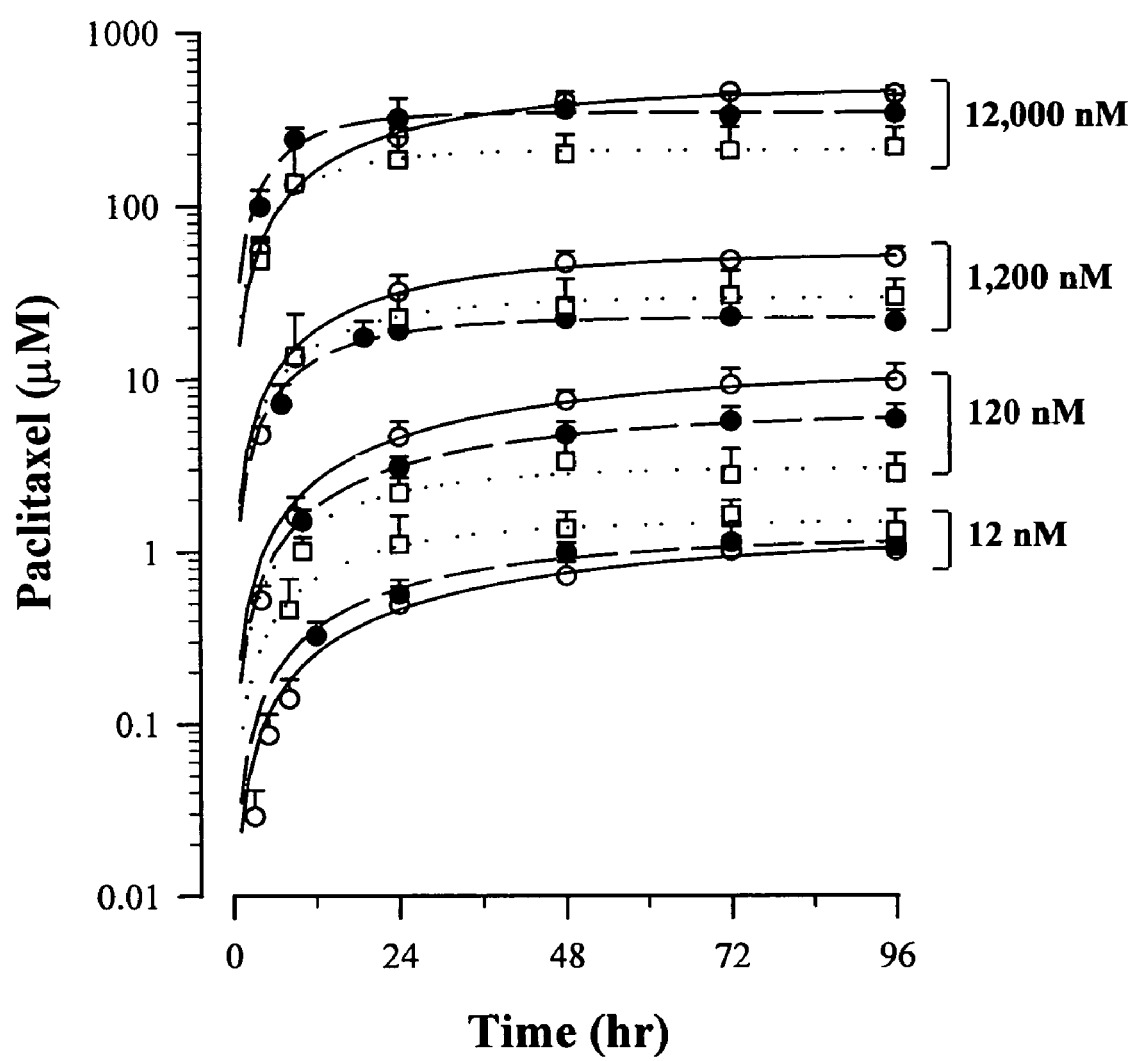
FIG. 1 is a line graph depicting the kinetics of paclitaxel uptake in patient and xenograft tumor histocultures. Patient head and neck tumors are represented by ●, patient ovarian tumors are represented by □, and FaDu xenograft tumors are represented by ○.

The invention, at least in part, is directed to methods for enhancing delivery of therapeutic agents, such as macromolecules and drugs, into the interior of multilayer tissues, such as solid tissues or tumors. The method initially uses an apoptosis inducing agent, such as paclitaxel, in doses which create channels within the tissues, and enhance the penetration of therapeutic agents to the interior of the tissue. Current methods of treating tissues are often not effective because the therapeutic agents are not delivered to the interior of the tissue. By using the methods and the compositions of the current invention, therapeutic agents can be delivered to the interior of the tissue.

At least in part, the invention pertains to the penetration of therapeutic drugs into tissues and tumors of a patient, by treating the tissue or tumor with an apoptosis inducing agent such that the permeability of the tissue or tumor to a therapeutic agent is enhanced. The therapeutic agent can be a protein bound drug, a chemotherapeutic agent, a gene therapy construct, or another agent which may be advantageously delivered to the interior of a tissue, such as a tumor.

In one embodiment, the invention pertains to a method for delivering a therapeutic agent to tissue of a patient. The method includes administering an apoptosis inducing agent to the patient, and allowing sufficient time for the apoptosis inducing agent to induce apoptosis in the tissue of the patient.

I. Definitions

Before further description of the invention, certain terms employed in the specification, examples and appended claims are, for convenience, collected here.

The term "apoptosis inducing agent" includes agents which induce apoptosis in cells, e.g., tumor cells. Cells, including cancer cells, can be induced to undergo programmed cell death, also known as apoptosis. Apoptosis is characterized by the selective programmed destruction of cells into relatively small fragments with DNA becoming highly fragmented (i.e. the resulting fragments typically have no more than about 200 bases). During apoptosis, cell shrinkage and internucleosomal DNA cleavage occurs, which results in the fragmentation of the DNA. Eventually the cell disintegrates into small fragments. Examples of apoptosis inducing agents include agents such as paclitaxel, doxorubicin, vincristine, vinblastine, vindesine, vinorelbin, taxotere (DOCETAXEL), topotecan, camptothecin, irinotecan hydrochloride (CAMPTOSAR), etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (ARA-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (ARA-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (Carmustine), melphalan, thiotepa, busulfan, chlorambucil, plicamycin, dacarbazine, ifosfamide phosphate, cyclophosphamide, nitrogen, mustard, uracil mustard, pipobroman, 4-ipomeanol, dihydrolenperone, spiromustine, geldanamycin, cytochalasins, depsipeptide, Lupron, ketoconazole, tamoxifen, goserelin (Zoledax), flutamide, 4'-cyano-3-(4-fluorophenylsulphonyl)-2-hydroxy-2-methyl-3'-(trifluoromethyl) propionanilide, Herceptin, anti-CD20 (Rituxan), interferon, alpha, interferon beta, interferon gamma, interleukin 2, interleukin 4, interleukin 12, tumor necrosis factors, and radiation.

The language "chemotherapeutic agent" includes agents such as drugs which can advantageously be administered to the tissue, such as anti-tumor drugs such as paclitaxel, doxorubicin, and other drugs which have been known to affect tumors. It also includes agents which modulate other states which are related to tissues which can be permeabilized using the methods and compositions of the invention. The chemotherapeutic agent can be, for example, a steroid, an antibiotic, or another pharmaceutical composition. Examples of chemotherapeutic agents include agents such as paclitaxel, doxorubicin, vincristine, vinblastine, vindesine, vinorelbin, taxotere (DOCETAXEL), topotecan, camptothecin, irinotecan hydrochloride (CAMPTOSAR), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (ARA-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (ARA-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldanamycin, cytochalasins, depsipeptide, Lupron, ketoconazole, tamoxifen, goserelin (Zoledax), flutamide, 4'-cyano-3-(4-fluorophenylsulphonyl)-2-hydroxy-2-methyl-3'-(trifluoromethyl) propionanilide, Herceptin, anti-CD20 (Rituxan), interferon alpha, interferon beta, interferon gamma, interleukin 2, interleukin 4, interleukin 12, tumor necrosis factors, and radiation.

The term "delivering" refers to making the therapeutic agent available to the interior of the tissue (e.g., tumor) to be treated such that the therapeutic agent is capable of having a; therapeutic effect on the interior of the tissue and includes, for example, contacting the tissue with the agent. The term "delivering" is intended to include administering the therapeutic agent to the patient as a separate dose (after administration of the apoptosis inducing agent), as well as administering the therapeutic agent to the patient together with (i.e., at the same time as or in the same dose as) the apoptosis inducing agent, wherein the therapeutic agent is formulated such that the tissue is contacted with the therapeutic agent after the sufficient time has elapsed for apoptosis to occur in the interior of the tissue (i.e., the therapeutic agent is delivered to the tissue after sufficient time has elapsed for apoptosis to occur).

The term "dose" refers to an amount of an apoptosis inducing agent or a therapeutic agent which is sufficient to perform its intended function, e.g., induce apoptosis and treat the tissue, respectively. In one embodiment, the dose of the apoptosis inducing agent may be, for example, between about 0.01 nM to about 1000 nM over about 0.01 to about 5.0 hours, between about 0.1 nM to about 500 nM over about 0.1 to about 4.0 hours, between about 1 nM to about 250 nM over about 0.5 to about 3.0 hours, between about 10 nM to about 150 nM over about 0.5 to about 2.0 hours, between about 30 nM to about 100 nM over about 0.75 to about 1.5 hours, between about 40 nM to about 70 nM over about 1 hour, and, advantageously, about 50 nM of paclitaxel over about 1 hour. The dose of the therapeutic agent can be, for example, administered for three hours, starting 24 hour after administration of the apoptosis-inducing agent. The target concentration of the therapeutic agent, can be, for example, about 50 nM. In another embodiment, the dose of the apoptosis inducing agent, can be, for human patients about one-half of the usual clinical dose (135–225 mg/m$^2$), administered by intravenous infusion over about, for example, 3 hours. The dose of the therapeutic agent can be, for example, the remaining one-half of the usual clinical dose, and could be administered, for example, between 16 to 30 hour after administration or delivery of the dose of the apoptosis inducing agent.

The term "gene therapy construct" includes constructs useful for gene therapy purposes, in treatments for either genetic or acquired diseases, e.g. cancer. The general approach of gene therapy involves the introduction of nucleic acid into cells such that one or more gene products encoded by the introduced genetic material are produced in the cells to restore or enhance a functional activity. For reviews on gene therapy approaches see Anderson, W. F. (1992) *Science* 256:808–813; Miller, A. D. (1992) *Nature* 357:455–460; Friedmann, T. (1989) *Science* 244:1275–1281; and Cournoyer, D., et al. (1990) *Curr. Opin. Biotech.* 1:196–208.

Genes of particular interest to be expressed in cells of a subject for treatment of genetic or acquired diseases include those encoding adenosine deaminase, Factor VIII, Factor IX, dystrophin, β-globin, LDL receptor, CFTR, insulin, erythropoietin, anti-angiogenesis factors, growth hormone, glucocerebrosidase, β-glucouronidase, α1-antitrypsin, phenylalanine hydroxylase, tyrosine hydroxylase, ornithine transcarbamylase, arginosuccinate synthetase, UDP-glucuronysyl transferase, apoA1, TNF, soluble TNF receptor, interleukins (e.g., IL-2), interferons (e.g., α- or γ-IFN) and other cytokines and growth factors. Cells types which can be modified for gene therapy purposes include tumor cells, hematopoietic stem cells, myoblasts, hepatocytes, lymphocytes, skin epithelium and airway epithelium. For further descriptions of cell types, genes and methods for gene therapy see e.g., Wilson, J. M et al. (1988) *Proc. Natl. Acad. Sci. USA* 85:3014–3018; Armentano, D. et al. (1990) *Proc. Natl. Acad. Sci. USA* 87:6141–6145; Wolff, J. A. et al. (1990) *Science* 247:1465–1468; Chowdhury, J. R. et al. (1991) *Science* 254:1802–1805; Ferry, N. et al. (1991) *Proc. Natl. Acad. Sci. USA* 88:8377–8381; Wilson, J. M. et al. (1992) *J. Biol. Chem.* 267:963–967; Quantin, B. et al. (1992) *Proc. Natl. Acad. Sci. USA* 89:2581–2584; Dai, Y. et al. (1992) *Proc. Natl. Acad. Sci. USA* 89:10892–10895; van Beusechem, V. W. et al. (1992) *Proc. Natl. Acad. Sci. USA* 89:7640–7644; Rosenfeld, M. A. et al. (1992) *Cell* 68:143–155; Kay, M. A. et al. (1992) *Human Gene Therapy* 3:641–647; Cristiano, R. J. et al. (1993) *Proc. Natl. Acad. Sci. USA* 90:2122–2126; Hwu, P. et al. (1993) *J. Immunol.* 150:4104–4115; and Herz, J. and Gerard, R. D. (1993) *Proc. Natl. Acad. Sci. USA* 90:2812–2816.

Gene therapy applications of particular interest in cancer treatment include overexpression of a cytokine gene (e.g., TNF-α) in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multidrug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant ICp4 mutants for HSV (see e.g., Balboni, P. G. et al. (1993) *J. Med. Virol.* 41:289–295; Liem, S. E. et al. (1993) *Hum. Gene Ther.* 4:625–634; Malim, M. H. et al. (1992) *J. Exp. Med.* 176:1197–1201; Daly, T. J. et al. (1993) *Biochemistry* 32:8945–8954; and Smith, C. A. et al. (1992) *Virology* 191:581–588), expression of trans-dominant negative envelope proteins, such as env mutants for HIV (see e.g., Steffy, K. R. et al. (1993) *J. Virol.* 67:1854–1859), intracellular expression of antibodies, or fragments thereof, directed to viral products ("internal immunization", see e.g., Marasco, W. A. et al. (1993) *Proc. Natl. Acad. Sci. USA* 90:7889–7893) and expression of soluble viral receptors, such as soluble CD4. Additionally, the system of the invention can be used to conditionally express a suicide gene in cells, thereby allowing for elimination of the cells after they have served an intended function.

The term "liposomes" or "lipid vesicles" refer to substantially spherical structures made of materials having a high lipid content in which the lipids are organized in the form of lipid bilayers. Unilamellar vesicles have a single lipid bilayer surrounding an amorphous central cavity which can encapsulate an aqueous volume. Unilamellar vesicles can be prepared as either large unilamellar vesicles (LUVs; diameter greater than about 1μ) or small unilamellar vesicles (SUVs; diameter less than about 0.2 μm). Multilamellar vesicles (MLVs) have many onion-like shells of lipid bilayers. Because of their high lipid content, MLVs have use for carrying certain small lipophilic molecules but have a low carrying capacity for aqueous material. Paucilamellar vesicles (PLVs) have about two-ten bilayers arranged in the form of substantially spherical shells separated by aqueous layers surrounding a central cavity free of lipid bilayers. PLVs can encapsulate both aqueous and hydrophobic material and thus can carry a wide variety of materials. Unilamellar vesicles composed of a single bilayer of phospholipids and/or glycolipids are the most commonly used lipid vesicles for modeling of cell membrane structures since phospholipids are the primary structural component of natural membranes, including the outer cell membrane. Liposomes (e.g., phospholipid vesicles), can be used as carrier vehicles for delivering biologically active materials to tissues using the methods of the invention. For reviews of phospholipid vesicle-mediated transfer of materials see Mannino, *BioTechniques,* 6:682 (1988); Litzinger, D. C. *Biochim. et Biophys. Acta,* 1113:201 (1992). Methods for preparing liposomes as carrier vesicles for delivery of biologically active materials are known in the art (see, for example, U.S. Pat. No. 4,522,811).

The term "locally" includes administration, e.g., injection, directly into the tissue to be treated. Examples of local treatment include intratumoral and intralesional injection.

The term "locoregionally" includes administration both locally and regionally. For example, the compound may be administered in the fluid surrounding the tissues and directly injected into the tissues, e.g., intraperitoneal treatment of ovarian cancer, intravesical instillation of drug into urinary bladder for the treatment of diseased bladder, intraprostatic injection, intrahepatic infusion, perfusion of isolated organs (e.g., lung), intrathecal treatment of brain tumors, implants of drug release devices in brain for the treatment of brain cancer, and intralesional injection (e.g., into a skin lesion or a tumor). Locoregional treatments may also apply to other diseases, e.g., viral or bacterial infection, interstitial cystitis.

The term "microparticles" includes particles which comprise apoptosis inducing agents, therapeutic agents or other substances which can be advantageously delivered using methods of the invention to the interior of a tissue, e.g., a tumor. The term refers to particles of about 0.1 μm to about 100 μm, about 0.5 μm to about 50 μm, 0.5 μm to about 20 μm in size, advantageously, particles of about 1 μm to about 10 μm in size, about 5 μm in size, or mixtures thereof. The microparticles may comprise macromolecules, gene therapy constructs, chemotherapeutic agents, or protein bound drugs, for example. Typically microparticles can be administered locally, locoregionally, or regionally, for example.

The term "nanoparticles" includes particles which comprise apoptosis inducing agents, therapeutic agents or other substances which can be advantageously delivered using methods of the invention to the interior or a tissue, e.g., a tumor. The term refers to particles of about 0.1 nm to about 1 μm, 1 nm to about 1 μm, about 10 nm to about 1 μm, about 50 nm to about 1 μm, about 100 nm to about 1 μm, about 250–900 nm in size, or, advantageously, about 600–800 nm. The nanoparticles may comprise macromolecules, gene therapy constructs, chemotherapeutic agents, or protein bound drugs, for example. Typically, nanoparticles can be administered to a patient via local, locoregional, regional, or systemic administration. In one embodiment, the nanoparticles may comprise cross-linked gelatin.

The term "patient" includes animals which can be treated using the methods of the invention. Examples of animals include mammals, such as mice, rabbits, rats, horses, goats, dogs, cats, pigs, cattle, sheep, and primates (e.g. chimpanzees, gorillas, and, preferably, humans). In a further embodiment, the patient is a cancer patient, e.g., a human suffering from cancer.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients; such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In one embodiment, the pharmaceutically acceptable carrier is suitable for intravenous administration. In another embodiment, the pharmaceutically acceptable carrier is suitable for locoregional injection.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted-into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.)

The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The term "protein bound drug" includes drugs bound to or capable of binding to proteins. Examples of protein bound drugs include paclitaxel, doxorubicin, cisplatin, carboplatin, oxaliplatin, vinca alkaloids, suramin, amitriptyline, amphotericin B, cefazolin, chlorothiazide, chlorpromazine, clindamycin, clofibrate, depsipeptide, desipramine, diazepam, dicloxacillin, digitoxin, doxycycline, furosemide, heparin, indomethacin, lorazepam, nafcillin, nortriptyline, phenyloin, prazosin, prednisolone, propranolol, protriptyline, rifampin, sulfisoxazole, warfarin.

The term "quick-release formulation" refers to a formulation of a drug, wherein the drug is delivered to a site of interest in an already activity form or a form that becomes active, in a relatively short period of time, e.g., within one or a few hours and includes formulations which allow the apoptosis inducing agent to be released in a dose of about 50 nM or more over about a 1 hour time. Examples of quick-release formulations include micro- and nanoparticle formulations. Methods used to prepare these formulation are described in Example 5.

The term "regionally" includes administration to a region of tissue where the tissue to be treated is located, e.g., intraperitoneal administration for the peritoneal organs (such as the bladder, ovaries, etc); intracranial administration for the brain; intra-spinal administration for spinal column tissue; intra peri-cardially for the cardiac tissue; and the like.

The term "simultaneously" includes administrations which occur together. In one embodiment, the therapeutic agent and the apoptosis inducing agent are formulated together. In such an embodiment, the apoptosis agent is typically in a quick formulation and the therapeutic agent is typically in a slow release formulation, such that the therapeutic agent is released, for example, about sixteen to twenty four hours after the apoptosis inducing agent.

The term "slow-release formulation" refers to a formulation of a drug wherein the drug is delivered to a site of interest for a sustained period of time and includes formulations which release the therapeutic agent after a sufficient time has elapsed for the apoptosis inducing agent to induce apoptosis. In one embodiment, the slow release formulation releases the therapeutic agent in about six to about 120 hours after administration, about six to 96 hours after administration, about six to about seventy two hours after administration, about six to about forty-eight hours after administration, about twelve to about thirty six hours after administration, about twelve to about thirty hours after administration, or, advantageously, about sixteen to about twenty four hours after administration.

The term "solid tissue cells" describes the cells that comprise a solid tumor or tissue and include, but are not limited to, "solid tumor cells." They includes cells in the outer or exterior cell layers which can be treated with an apoptosis inducing agent such that a therapeutic agent can be delivered to the interior of the tumor or tissue, and the inner cell layers of a multi-layer tissue. Solid tumor or tissue cells can be derived from epithelial or non-epithelial lineages. The term "solid tumor cells" includes cells that comprise a solid tumor, and also includes that cells in the outer or exterior cell layers.

The term "sufficient time" includes the length of time which is necessary for the apoptosis inducing agent to induce apoptosis, such that the tissue is permeabilized to the therapeutic agent. For example, the sufficient time may be when the density of the epithelial, exterior or solid tissue or tumor cells have been reduced, e.g., reduced by 1%, 2%, 3%, 4%, 5% 10%, 20%, 25%, 30%, 35%, 40%, 45%, 50% or greater. In another example, the sufficient time may be when apoptosis has been induced in some, e.g., 1%, 2%, 3%, 4%, 5%, 6%, 7%, 8%, 9%, 10%, 11%, 12%, 15%, 17%, 20% or more of the solid tissue cells. In Example 3, it has been shown that, in at least in certain situations, the sufficient time for a apoptosis inducing agent such as paclitaxel when administered at a dose of 50 nM over one hour, is about sixteen to twenty four hours. The sufficient time may vary according to the identity and the dose of the apoptosis inducing agent and can be determined using such methods as those described in the Examples.

In a further embodiment, the sufficient time is, for example, seventy two hours or more, seventy two hours or less, sixty hours or less, fifty five hours or less, fifty hours or less, forty five hours or less, forty hours or less, thirty five hours or less, thirty two hours or less, thirty hours or less, twenty seven hours or less, twenty four hours or less, twenty three hours or less, twenty two hours or less, twenty one hours or less, twenty hours or less, nineteen hours or less, eighteen hours or less, seventeen hours or less, sixteen hours or less, fifteen hours or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less.

The language "therapeutic agent" encompasses any agent that can confer a therapeutic benefit on a patient and includes gene therapy constructs, chemotherapeutic agents, antibiotics, macromolecules, and protein bound drugs. The language also includes any agents which can be delivered to the interior of the tissue using the methods described herein. In one embodiment, the therapeutic agent is paclitaxel or doxorubicin, or analogues or derivatives thereof. In one embodiment, the therapeutic agent comprises the same active component as the apoptosis inducing agent. For example, both the apoptosis inducing agent and the therapeutic agent can be compounds such as, but not limited to, paclitaxel or doxorubicin. The therapeutic agent may be formulated as microparticles or nanoparticles. Other examples of therapeutic agents include macromolecules, such as, liposomes, nanoparticles, plasmid, viral vectors, non-viral vectors, chemotherapeutics, and oligonucleotides.

The term "tissue" includes both normal mammalian tissues such as liver, muscle (e.g., cardiac, skeletal, or smooth muscle), skin, neuronal, and adipose tissue, as well as both benign and cancerous tumors.

The term "tumor" refers to abnormally growing tissue of any tissue type and includes both benign and malignant tumors, such as cancerous tumors. Examples of cancerous tumors include sarcomas, carcinomas, adenocarcinomas, lymphomas, and leukemias. The cancerous tumor may comprise metastatic lesion. It also includes any other tumors which can be advantageously treated using the methods and compositions of the invention. The cancerous tumor may be, for example, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, colon carcinoma, rectal cancer, pancreatic cancer, breast cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, lung carcinoma, small cell lung carcinoma; non-small cell lung carcinoma, bladder carcinoma, epithelial carcinoma, glioma, astrocytoma, medulloblastoma, craniopharyngioma, ependymoma, pinealoma; hemangioblastoma, acoustic neuroma, oligodendroglioma, meningioma, melanoma, neuroblastoma, retinoblastoma, leukemia, lymphoma, or Kaposi's sarcoma.

The term "tumor suppressor genes" include genes known to suppress tumors, e.g., tumors which are treatable by using the methods of the invention. Examples of tumor suppressor genes include, for example, p53.

II. Methods of the Invention

In one embodiment, the invention pertains to a method for delivering a therapeutic agent to tissue (e.g., the interior of a multilayer tissue) of a patient, e.g., a mammal, e.g., a human. The method includes administering an apoptosis inducing agent to the patient, allowing sufficient time for the apoptosis inducing agent to induce apoptosis in the patient's tissue, and delivering a therapeutic agent to the tissue. The tissue can be, for example, liver, muscle (e.g., cardiac, skeletal, or smooth muscle), skin, neuronal, or adipose tissue, or a tumor, such as a brain, breast, ovarian, bladder, prostate, colon, lung, liver, or uterine tumor. The apoptosis agent can be administered systemically, locally, regionally, or any combination thereof, such as both locally and regionally (locoregionally). In a further embodiment, the method further comprises obtaining the apoptosis inducing agent prior to administration to the patient.

In a further embodiment, the apoptosis inducing agent is paclitaxel or doxorubicin. The therapeutic agent can be a gene therapy construct, a chemotherapeutic agent, a protein bound drug or; an antibiotic.

In a second further embodiment, the sufficient time and/or dosage is sufficient to reduce the density of the epithelial, exterior, or solid cells of the tissue. For example, the density of the solid tissue cells may be reduced by about 1%, 2%, 3%, 4%, 5%, 6%, 7%, 8%, 9%, 10%, 11%, 12%, 13%, 14%, 15%, 16%, 17,%, 18%, 19%, 20%, 25%, 30%, 35%, 40%, 45%, 50% or greater, over a period, for example, of thirty two hours or less, thirty hours or less, twenty seven hours or less, twenty four hours or less, twenty three hours or less, twenty two hours or less, twenty one hours or less, twenty hours or less, nineteen hours or less, eighteen hours or less, seventeen hours or less, sixteen hours or less, fifteen hours or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less.

In another example, the density of the solid tissue cells may be reduced by about 0.1% to about 50%, about 1% to about 45%, about 2% or about 45%, about 1% to about 40%, 5% to about 40%, 10% to about 40%, 20% or about 40%, 25% to about 40%, or about 30% to about 35%, over a period, for example, of thirty two hours or less, thirty hours or less, twenty seven hours or less, twenty four hours or less, twenty three hours or less, twenty two hours or less, twenty one hours or less, twenty hours or less, nineteen hours or less, eighteen hours or less, seventeen hours or less, sixteen hours or less, fifteen hours or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less.

In another, the time is sufficient to induce apoptosis in about 1%, 2%, 3%, 4%, 5%, 6%, 7%, 8%, 9%, 10%, 11%, 12%, 13%, 14%, 15%, 20%, 25% or more of the solid tissue cells, over a period, for example, of thirty two hours or less, thirty hours or less, twenty seven hours or less, twenty four hours or less, twenty three hours or less, twenty two hours or less, twenty one hours or less, twenty hours or less, nineteen hours or less, eighteen hours or less, seventeen hours or less, sixteen hours or less, fifteen hours or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less.

In another embodiment, the time and/or the dosage is sufficient to induce apoptosis in about 1% to about 25% of the solid tissue cells, or, alternatively, about 1% to about 20%, about 1% to about 17%, about 1% to about 15%, about 1% to about 14%, about 5% to about 13%, about 5% to about 12%, about 1% to about 10%, over a period, for example, of thirty two hours or less, thirty hours or less, twenty seven hours or less twenty four hours or less, twenty three hours or less, twenty two hours or less, twenty one hours or less, twenty hours or less, nineteen hours or less, eighteen hours or less, seventeen hours or less, sixteen hours or less, fifteen hours, or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less. Apoptosis of the cells as well as their density can be measured using techniques discussed in Examples 1, 2, and 3.

In a third further embodiment, the apoptosis inducing agent is also the therapeutic agent. However, in this case, the therapeutic agent is typically administered in a separate dose or in a slow-release form.

In a fourth further embodiment, the apoptosis inducing agent and the therapeutic agent are administered simultaneously. In this embodiment, the therapeutic agent is typically a slow-release formulation that releases the therapeutic agent after sufficient time to allow for the apoptosis inducing agent to induce apoptosis in the tissue of the patient.

In a yet another further embodiment, the apoptosis agent and the therapeutic agent are administered sequentially. In this method, the therapeutic agent is administered as a separate dose after sufficient time to allow for the apoptosis inducing agent to induce apoptosis in the tissue of the patient.

In a second embodiment, the invention pertains to a method for delivering a therapeutic agent to a patient's tumor (e.g., a cancerous or benign tumor). The method includes administering a dose of an apoptosis inducing agent to a patient, allowing sufficient time for the apoptosis inducing agent to induce apoptosis in the tumor; and delivering a dose of a therapeutic agent to said patient. The tumor may be, for example, a brain, breast, ovarian, bladder, prostate, colon, lung, liver, or uterine tumor. Examples of the apoptosis inducing agent include paclitaxel and doxorubicin. In a further embodiment, the method also comprises obtaining the apoptosis inducing agent.

In a further embodiment, the dose of the apoptosis inducing agent is sufficient to reduce the density of epithelial, exterior, or solid tumor cells, such that the therapeutic agent can be delivered to the interior of the tumor. For example, the dosage of the apoptosis inducing agent is sufficient to reduce the density of the cells, e.g., by about 1%, 2%, 3%, 4%, 5%, 6%, 7%; 8%, 9%, 10%, 15%, 20%, 25%, 30%, 35%, 40%, 45% or greater, over a period, for example, of thirty two hours or less, thirty hours or less, twenty seven hours or less, twenty four hours or less, twenty three hours or less, twenty two hours or less, twenty one hours or less, twenty hours or less, nineteen hours or less, eighteen hours or less, seventeen hours or less, sixteen hours or less, fifteen hours or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less.

In another further embodiment, the apoptosis inducing agent induces apoptosis in about 1%, 2%, 3%, 4%, 5%, 6%, 7%, 8%, 9%, 10%, 12%, 15%, 20%, 25% or more of the solid tissue cells, over a period, for example, of thirty two hours or less, thirty hours or less, twenty seven hours or less, twenty four hours or less, twenty three hours or less, twenty two hours or less, twenty one hours or less, twenty hours or less, nineteen hours or less, eighteen hours or less, seventeen hours or less, sixteen hours or less, fifteen hours or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less. In one particular instance when the apoptosis inducing agent is paclitaxel, the sufficient time can be, for example, between about 16 to about 24 hours, when it is administered at a dose of about, 50 nM over about 1 hour.

In a second further embodiment, the apoptosis inducing agent is also the therapeutic agent. However, in this case, the therapeutic agent is either administered in a separate dose or in a slow-release form of the apoptosis inducing agent. Examples of apoptosis inducing agents which are also effective as therapeutic agents include, for example, paclitaxel and doxorubicin.

In a third further embodiment, the therapeutic agent comprises a gene therapy construct, a protein bound drug, a chemotherapeutic agent, or an antibiotic.

In a fourth further embodiment, the apoptosis inducing agent and/or the therapeutic agent can each be administered systemically, regionally, locoregionally, or locally. In an advantageous embodiment, the apoptosis inducing agent and/or the therapeutic agent are administered with a one or more pharmaceutically acceptable carriers. For example, the agents can be formulated in a manner suitable intravenous injection.

In yet another embodiment, the invention features a method for delivering a chemotherapeutic agent to a tumor in a patient, for example, a human (e.g., a cancer patient). The method includes administering a dose of an apoptosis inducing agent locally or regionally to a patient, allowing sufficient time for said apoptosis inducing agent to induce apoptosis in the tumor, and delivering a dose of a chemotherapeutic agent to said patient. In a further embodiment, the tumor is a cancerous tumor, e.g., a brain, breast, ovarian, bladder, prostate, colon, lung, liver, or uterine tumor. In a further embodiment, the invention also comprises the step of obtaining the apoptosis inducing agent.

In a second further embodiment, the apoptosis inducing agent comprises paclitaxel, doxorubicin, or another effective apoptosis inducing agent.

In a third further embodiment, the sufficient time is sufficient for the reduction of the density of the solid tissue cells such that the therapeutic agent can be delivered to the interior of the tumor. For example, the sufficient time may be sufficient to reduce the density of the cells by about 5%, 10%, 15%, 20%, 30%, 35% or more, over a period of thirty two hours or less, thirty hours or less, twenty seven hours or less, twenty four hours or less, twenty three hours or less, twenty two hours or less, twenty one hours or less, twenty hours or less, nineteen hours or less, eighteen hours or less, seventeen hours or less, sixteen hours or less, fifteen hours or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less. In yet another further embodiment, the sufficient time is sufficient to induce apoptosis in the solid tissue cells, such that the therapeutic agent can be delivered to the interior of the tumor. For example, the sufficient time can be sufficient to induce apoptosis of about 1%, 2%, 3%, 4%, 5%, 6%, 7%, 8%, 9%, 10%, 11%, 12%, 13%, 14%, 15%, 16%, 17%, 18%, 19%, or 20% or more of the solid tissue cells, over a period, for example, of thirty two hours or less, thirty hours or less, twenty seven hours or less, twenty four hours or less, twenty three hours or less, twenty two hours or less, twenty one hours or less, twenty hours or less, nineteen hours or less, eighteen hours or less, seventeen hours or less, sixteen hours or less, fifteen hours or less, fourteen hours or less, thirteen hours or less, twelve hours or less, eleven hours or less, ten hours or less, nine hours or less, eight hours or less, seven hours or less, six hours or less, five hours or less, four hours or less, three hours or less, two hours or less, or one hour or less.

In a fourth further embodiment, the apoptosis inducing agent is also the chemotherapeutic agent. However, in this case, the chemotherapeutic agent is either administered as a separate dose or in a slow-release form.

In a fifth further embodiment, the apoptosis agent and/or the therapeutic agent are administered with a pharmaceutically acceptable carrier, e.g., a carrier suitable for systemic, regional, locoregional, or local administration. The carrier may be suitable for intravenous injection.

In a sixth further embodiment, the apoptosis inducing agent and the therapeutic agent are administered simultaneously. In this embodiment, the therapeutic agent is slow-release formulated such that it is released after sufficient time for the apoptosis inducing agent to induce apoptosis.

In a seventh further embodiment, the apoptosis agent and the therapeutic agent are administered sequentially. In this embodiment, the therapeutic agent is administered after sufficient time, to allow the apoptosis inducing agent to induce apoptosis in the tissue of the patient.

In another embodiment, the invention pertains to a method for delivering a dose of a therapeutic agent to tissue of a patient.

The method includes administering a dose of an apoptosis inducing agent to the patient, wherein the dose of the apoptosis inducing agent either:

(i) does not comprise the dose of the therapeutic agent; or (ii) comprises the dose of the therapeutic agent in a slow release formulation;

allowing sufficient time for the apoptosis inducing agent to induce apoptosis in the tissue of the patient; and (a) when the dose of the apoptosis inducing agent does not comprise the dose of the therapeutic agent, administering the dose of the therapeutic agent to the patient such that the dose of therapeutic agent is delivered to the tissue of the patient; or (b) when the dose of the apoptosis inducing agent comprises the dose of the therapeutic agent in a slow release formulation, allowing sufficient time for the therapeutic agent to be released in the tissue such that the dose of the therapeutic agent is delivered to the tissue of the patient.

The invention also pertains to a method for treating an ovarian tumor, comprising administering a dose of an apoptosis inducing agent, such as paclitaxel or doxorubicin locoregionally, regionally, or locally to a patient and allowing for sufficient time for apoptosis agent to induce apoptosis, and delivering the therapeutic agent. In a further embodiment, the apoptosis inducing agent is paclitaxel, the dose is 50 nM over 1 hour, and the sufficient time is 16 to 24 hours.

The invention also pertains to a method for treating a breast cancer tumor, comprising administering a dose of an apoptosis inducing agent, such as paclitaxel or doxorubicin locoregionally, regionally, or locally, to a patient and allowing for sufficient time for the apoptosis agent to induce apoptosis, and delivering the therapeutic agent. In a further embodiment, the apoptosis inducing agent is doxorubicin, and the dose is 5:M for 1 to 4 hour, and the sufficient time is 16–30 hours.

III. Pharmaceutical Compostions of the Invention

The invention also pertains to a composition for delivering a therapeutic agent to a patient. The composition includes a quick release formulation of an apoptosis inducing agent, a slow release formulation of a therapeutic agent, and a pharmaceutically acceptable carrier.

In a further embodiment, the apoptosis inducing agent is paclitaxel. For example, one quick release formulation advantageously releases about 50 nM of paclitaxel over about 1 hour or less.

In a second further embodiment, the apoptosis inducing agent is doxorubicin.

In a third further embodiment, the apoptosis inducing agent is provided in an amount sufficient to reduce the density of the tumor cells of a solid tumor by about 30% or greater, within about 16–24 hours after administration. The apoptosis inducing agent may also be provided in an amount sufficient to induce apoptosis in 10% or more of the tumor cells of a solid tumor, within about 16–30 hours after administration.

In a fourth further embodiment, the therapeutic agent is paclitaxel or doxorubicin, protein-bound drug, a chemotherapeutic agent; an antibiotic or a gene delivery construct, e.g., a gene delivery construct comprising a tumor suppressor gene, e.g., p53.

In a fifth further embodiment, the pharmaceutical composition is suitable for intravenous injection. The composition may also be suitable for local, locoregional, regional or systemic administration.

In another embodiment, the pharmaceutical composition may comprise one or more pharmaceutical acceptable carriers.

In yet another embodiment, the invention pertains to nanoparticles, which comprise a cross linked gelatin and a therapeutic agent or an apoptosis inducing agent, such as, for example, paclitaxel, or doxorubicin. In a further embodiment, the invention pertains to a compositions containing the nanoparticles and a pharmaceutically acceptable carrier. The carrier can be, for example, suitable for systemic, regional, locoregional, or local administration. In another embodiment, the invention pertains to a method of treating a patient comprising administering the nanoparticles of the invention. In one embodiment, the nanoparticles are about 500 to about 1 μm, or about 600 nm to about 800 nm in diameter.

The invention also pertains to microparticles comprising a therapeutic agent or an apoptosis inducing agent, such as paclitaxel or doxorubicin. In one embodiment, the microparticle is about 500 nm to about 100 μm, about 500 nm to about 50 μm, about 500 nm to about 25 μm, about 500 nm to about 20 μm, about 500 nm to about 15 μm, about 500 nm to about 10 μm, about 750 nm to about 10 μm, about 1 μm to about 10 μm, about 750 nm to about 7.5 μm, about 1 μm to about 7.5 μm, about 2 μm to about 7.5 μm, 3 μm to about 7 μm, or about 5 μm in diameter. In another embodiment, the invention pertains to a composition which comprises the microparticles and a pharmaceutically acceptable carrier. The pharmaceutically acceptable carrier may be, for example, suitable for administration to a patient locally, regionally, or locoregionally. The invention also pertains to a method for treating a patient, comprising administering to the patient microparticles of the invention and a pharmaceutically acceptable carrier. In a further embodiment, the administration can be local, regional, or locoregional.

In another embodiment, the invention features microparticle suitable for administration to a patient locally, regionally, or locoregionally, comprising paclitaxel, wherein said microparticle has a diameter of about 5 μm. In another further embodiment, the invention features microparticles suitable for administration to a patient locally, regionally, or locoregionally, comprising doxorubicin, wherein said microparticle has a diameter of about 5 μm.

The invention also pertains to a kit for the treatment of tumors. The kit contains an apoptosis inducing agent in a pharmaceutically acceptable carrier, a therapeutic agent in a pharmaceutically acceptable carrier, a container, and directions for using said apoptosis inducing agent and said therapeutic agent for the treatment of tumors. For example, a kit of the invention may comprise an apoptosis inducing agent and a therapeutic agent for subsequent intravenous injection. The kit may also provide the apoptosis inducing agent and/or the therapeutic agent formulated in dosages and carriers appropriately for local, locoregional, or regional administration.

Pharmaceutical compositions comprising compounds of the invention may contain wetting agents, emulsifiers and lubricants, such as sodium lauryl sulfate magnesium stearate, as well as coloring agents, release agents, coating agents, sweetening, flavoring and perfuming agents, and preservatives.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 per cent to about 30 per cent.

Methods of preparing these formulations/or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as, sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar—agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, rectally, intralesionally, intraorbitally, intracapsularly, directly instilled into a cavity, or by inhalation. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

These compounds may be administered to humans and other animals for therapy by any suitable route of administrations including orally, nasally, as by, for example, a spray, rectally, intravaginally, parenterally; intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed; the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable dose of a compound of the invention will be that amount of the compound which is the lowest dose effective to produce a therapeutic effect; i.e., treat a condition in a subject, e.g., cancer. Such an effective dose will generally depend upon the factors described above. Generally, intravenous and subcutaneous doses of the compounds of this invention for a patient, will range from about 0.0001 to about 100 mg per kilogram of body weight, more preferably from about 0.01 to about 10 mg per kg, and still more preferably from about 10 to about 4 mg per kg. If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

As set out above, certain embodiments of the present compounds can contain a basic functional group, such as amino or alkylamino, and are, thus, capable of forming pharmaceutically acceptable salts with pharmaceutically acceptable acids.

In other cases, the compounds of the present invention may contain one or more acidic functional groups and, thus, are capable of forming pharmaceutically acceptable salts with pharmaceutically acceptable bases.

EXEMPLIFICATION OF THE INVENTION

The invention is further illustrated by the following examples that should not be construed as limiting.

Materials and Methods:

Chemicals and Reagents:

Paclitaxel and doxorubicin were obtained from the Bristol Myers Squibb Co. (Wallingford, Conn.), the Pharmacia & Upjohn Co. (Milan, Italy), and/or the National Cancer Institute (Bethesda, Md.), and 3"-[$^3$H]paclitaxel (specific activity 19.3 Ci/mmol) from the National Cancer Institute. Cefotaxime sodium was purchased from Hoechst-Roussel Inc. (Somerville, N.J.); gentamicin from Solo Pak Laboratories (Franklin Park, Ill.); fetal bovine serum (FBS), Dulbecco's modified Eagle medium (DMEM), minimum essential medium (MEM), RPMI-1640, non-essential amino acids, L-glutamine and trypsin from GIBCO Laboratories (Grand Island, N.Y.); sterile pigskin collagen gel (Spongostan standard) from Health Designs Industries (Rochester, N.Y.); Solvable tissue gel solubilizer and Atomlight scintillation fluid from Dupont Biotechnology Systems (Boston, Mass.); Hyperfilm $^3$H from Amersham Life Science Inc. (Arlington Heights, Ill.); autoradiographic supplies from Kodak (Rochester, N.Y.); Cremophor EL from Sigma (St. Louis, Mo.); LKB 2208 Ultrofilm from Leica (Deerfield, Ill.), autoradiographic supplies from Kodak (Rochester, N.Y.), cryotome imbedding polymer (O.C.T.) was obtained from Miles Inc. (Ellchart, Ind.); and monoclonal antibody (JSB-1) and polyclonal antibody (ab-1) against Pgp from BioGenex (San Ramon, Calif.) and Oncogene (Cambridge, Mass.), respectively.

Animals

Male nu/nu balb/c mice, weighing 18–21 g, were purchased from the National Cancer Institute, male Copenhagen rats, weighing 190 to 210 g, from Harlan Biomedicals (Dawely, Ohio), and female nu/nu balb/c mice, weighing 18–22 g, from the National Cancer Institute. Animal care was provided by the Laboratory Animal Resources in our institution.

Tumor Procurement

Surgical specimens of patient tumors (i.e., prostate, head and neck, ovarian) were obtained via the Tumor Procurement Service at The Ohio State University Comprehensive Cancer Center. Prostate tumor specimens were placed in MEM, and head and neck and ovarian tumor specimens in Hanks balanced salt solution within 10 to 30 min after surgical excision, stored on ice and prepared for culturing within one hour after excision.

Establishment of Human Xenograft Tumors in Mice

Three human xenograft tumors, i.e., human pharynx FaDu tumor, human mammary MCF7 tumor, and the human prostate PC3 tumor, were used in the following three examples. FaDu cells were obtained from American Type Culture Collection (Rockville, Mass.). MCF7 cells were obtained from Dr. Kenneth Cowan at the National Cancer Institute. Cells were harvested from subconfluent cultures using trypsin and resuspended in fresh medium before plating. Cells with greater than 90% viability, as determined by trypan blue exclusion, were used for tumor implantation. Cells were centrifuged and resuspended in Matrigel (1:1 v/v). Matrigel is a solubilized tissue basement membrane preparation extracted from the Engelbreth-Holmswarm mouse tumor and has been shown to support the growth of human tumors in immunodeficient mice (Kleinman H et al. (1990) *Proc Am Assoc Cancer Res* 31:490–491). The tumor establishment was achieved by subcutaneously injecting $10^6$ cells (0.1–0.2 ml) with a 18 gauge needle at left and right sides of the upper back. The tumor was removed when it reached a size of 0.5 to 1 g and used for experiments.

Establishment of the MCF7 tumor was similar as described for the FaDu tumor, with the except that a sustained release pellet of 17-beta-estradiol was implanted subcutaneously behind the neck of a mouse. Tumors were harvested when the tumor reached a size of about 0.5 in two weeks.

The androgen-independent human prostate PC3 cells were maintained as xenograft tumors in male nude mice according to the previously published procedures (Pretlow et al., 1993; Nagabhushan et al., 1996). Briefly, minced tumor tissue mixed with the same volume of Matrigel was implanted into both flanks of the nude mice at 0.3 ml per site. Tumors were harvested when they reached a size of 1 g at about 1.5 to 2 months after implantation.

Histocultures

Patient tumors or xenograft tumor specimens were processed as previously described (Kuh, et al. (1999) *J. Pharmcol. Exper. Therap.* 290:871–880). The specimens were washed with culture medium for three times and dissected into about 1 mm$^3$ fragments under sterile conditions. The culture medium consisted of a 1:1 mixture of MEM/DMEM for patient tumors, MEM for FaDu xenografts, and RPMI1640 for PC3 xenografts, supplemented with 9% heat-inactivated FBS, 2 mM glutamine, 0.1 mM non-essential amino acids (only for MEM/DMEM), 90:g/ml gentamicin and 90:g/ml cefotaxime sodium. Five histoculture fragments were placed on a 1 cm$^2$ piece of presoaked collagen gel and incubated with 4 ml culture medium in 6-well plates. After 2 to 4 days, tumor histocultures were used to study the kinetics of drug penetration.

Example 1

Determinants of Paclitaxel Penetration and Accumulation in Human Solid Tumors This study was performed using head and neck tumors from human patients and the human pharynx FaDu xenograft tumors maintained in athymic mice. The study used [$^3$H]paclitaxel. The penetration of paclitaxel into tumor histocultures was visualized using autoradiography and the drug concentration tumor tissues was measured using liquid scintillation counting.

Methods to Study Drug Uptake and Efflux in Histocultures

Tumor histocultures were incubated with 4 ml of culture medium containing 12 to 12,000 nM of mixture of radiolabeled and unlabeled paclitaxel. The final concentration of [$^3$H]paclitaxel was 2.6 nM at 0.05 μCi/ml or 5.2 nM at 0.1 μCi/ml. These paclitaxel concentrations are within the range of clinical achievable concentrations in plasma (i.e. up to 13,000 nM, Kearns et al. (1995) *Sem Oncol* 22 (Suppl. 6):16–23). For the efflux study, tumor histocultures were incubated with paclitaxel for 24 hr, which was the longest time before substantial apoptosis occurs (Au J L S et al. (1998) *Cancer Res* 58:2141–2148), and then transferred to new plates and maintained in drug-free medium. At predetermined times, 100 μl of medium was taken from each well and the histocultures were removed from the plates. The histocultures were blot-dried on a filter paper and their weights were measured. One hundred 1 of medium or tumor samples were mixed with 0.5 ml of Solvable tissue/gel solubilizer, incubated at 50° C. in an oven overnight, and analyzed for total radioactivity using liquid scintillation counting. A preliminary study determined that 95% of the radioactivity in culture medium, analyzed by high pressure liquid chromatographic fractionation using a previous described method (Royer I et al. (1995) *Rapid Commun Mass Spectrom* 9:495–502), was represented by paclitaxel and its epimerization product, 7-epitaxol. The ratio of 7-epitaxol to paclitaxel, in culture medium containing FaDu cells, was affected by the incubation time and the drug concentration in the medium, increasing from 2% at 3 hr to 7% in 24 hr and from 7% at 100 nM to 25% at 5,000 nM after 24 hr. Because 7-epitaxol has similar microtubule binding affinity and cytotoxicity as paclitaxel (Ringel I et al. (1987) *J Pharmacol Exp Ther* 242:692–698), the total radioactivity was expressed in paclitaxel equivalents. Drug concentration in tissue was calculated as (drug amount) divided by (tissue weight) and was expressed in molar terms.

For each tumor category, i.e. patient head and neck tumors, patient ovarian tumors, and FaDu xenograft tumors, three tumors were used per experiment, and 30 to 35 tumor histocultures were used for each concentration and each time point. The study design of experiments using patient tumors was dictated by the size of the specimens. On some occasions, specimens from an individual patient were only sufficient to study drug uptake and efflux at one or more but not all drug concentrations. A total of 7 head and neck tumors and 3 ovarian tumors were used. For the FaDu xenograft tumor, specimens from individual animals were sufficiently large that each tumor was used for studying uptake and efflux at all four drug concentrations.

Accumulation of Paclitaxel in Tumor Histocultures

The increase of paclitaxel-concentration in histocultures of patient tumors (head and neck, ovarian) and xenograft tumor is depicted in FIG. 1 and in Table 1. For all three tumor types, the drug concentration in tumor histocultures increased with time, reaching a pseudo steady state between 48 to 72 hr, with <5% increase in the next 24 to 48 hr. During this time period, the drug concentration in the medium decreased by about 25%. Analysis of the mass balance indicates that about 90% of the dose was accounted for. The tumor-to-medium concentration ratios at steady state ranged from 20 to 120, indicating significant drug accumulation in tumors.

FIG. 1 and Table 1 show the results of an experiment designed to test the uptake of paclitaxel into histocultures of FaDu xenograft and patient tumors. The concentration-time profiles of paclitaxel in tumor histocultures obtained after incubation with different initial drug concentrations in culture medium ($C_{medium}$), as depicted in FIG. 1, were analyzed for the time for the tumor concentration to reach one-half of the pseudo steady state level ($T_{1/2,uptake}$) and for the tumor-to-medium concentration ratio at steady state. The statistical significance of the differences among patient (head and neck and ovarian, n=6) and FaDu (n=3) tumors, at equal initial medium concentrations, were analyzed by the two-tailed unpaired Student's t-test.

TABLE 1

| Tumor | Initial $C_{medium}$ (nM) | Steady state $C_{medium}$ (nM) | Steady state $C_{tumor}$ (:M) | Steady state $C_{tumor}$-to-$C_{medium}$ ratio | $T_{1/2,uptake}$ (h) | Mass balance (%) |
|---|---|---|---|---|---|---|
| Head and neck patient tumor | 12 | 10.9 ± 1.0 | 1.06 ± 0.21 | 97.8 ± 15.2 | 24.2 ± 3.4 | 91.2 ± 3.5 |
| | 120 | 83.0 ± 0.7 | 5.77 ± 1.52 | 64.5 ± 18.4 | 19.8 ± 4.5 | 83.8 ± 7.6 |
| | 1,200 | 925 ± 25 | 22.0 ± 6.2 | 23.1 ± 7.1 | 10.4 ± 3.8 | 87.5 ± 6.5 |
| | 12,000 | 9,870 ± 59 | 341 ± 125 | 34.8 ± 14.5 | 5.81 ± 2.31 | 91.5 ± 3.5 |
| Ovarian patient tumor | 12 | 10.6 ± 0.7 | 1.32 ± 0.31 | 109 ± 22 | 18.4 ± 9.6 | 89.3 ± 5.4 |
| | 120 | 86.4 ± 2.3 | 2.86 ± 1.28 | 32.8 ± 14.2 | 11.1 ± 6.6 | 84.5 ± 7.3 |
| | 1,200 | 870 ± 2.6 | 30.1 ± 11.7 | 32.3 ± 13.7 | 14.2 ± 7.3 | 85.2 ± 2.5 |
| | 12,000 | 10,500 ± 920 | 211 ± 80 | 19.8 ± 8.4 | 7.17 ± 3.81 | 93.3 ± 4.5 |
| FaDu xenograft | 12 | 9.09 ± 0.27 | 1.01 ± 0.21 | 124 ± 25 | 35.3 ± 2.0[a] | 92.5 ± 5.1 |
| | 120 | 89.7 ± 13.3 | 9.51 ± 2.88[a] | 1.15 ± 38[a] | 27.8 ± 3.7[a] | 86.5 ± 2.8 |
| | 1,200 | 887 ± 131 | 48.8 ± 6.6[a] | 53.7 ± 14.8[a] | 18.9 ± 3.2[a] | 89.4 ± 5.7 |
| | 12,000 | 8,910 ± 267 | 433 ± 15[a] | 48.5 ± 0.5[a] | 21.6 ± 6.9[a] | 90.2 ± 5.4 |

[a] $p < 0.05$.

The steady state paclitaxel concentration in tumors increased while the steady state tumor-to-medium concentration ratio decreased with the initial drug concentrations in culture medium, although the relationships were not linear. In general, $T_{1/2,uptake}$, which is the time to reach 50% of the pseudo steady state level, decreased with increasing initial medium concentration (p<0.01, regression analysis). These data indicate that drug accumulation is partly saturable, and show a more rapid attainment of steady state at higher initial extracellular drug concentration.

tical significance of the differences among patient (head and neck and ovarian, n=6) and FaDu (n=3) tumors, at equal initial medium concentrations, were analyzed using a unpaired t-test. Different units were used for the medium and tumor concentrations.

TABLE 2

| Tumor | Initial $C_{medium}$ (nM) | At 24 hr post-treatment | | | | At 72 hr post-treatment | | | | $T_{1/2,efflux}$ (h) |
|---|---|---|---|---|---|---|---|---|---|---|
| | | $C_{medium}$ (nM) | $C_{tumor}$ (:M) | $C_{tumor}$-to-$C_{medium}$ ratio | % remaining in tumor | $C_{medium}$ (nM) | $C_{tumor}$ (:M) | $C_{tumor}$-to-$C_{medium}$ ratio | % remaining in tumor | |
| Head and neck patient | 120 | 1.13 ± 0.17 | 1.70 ± 0.44 | 1560 ± 514 | 54.8 ± 3.1 | 1.32 ± 0.14 | 1.19 ± 0.50 | 880 ± 300 | 43.3 ± 16.3 | 7.45 ± 3.02 |
| | 1,200 | 7.69 ± 2.55 | 4.38 ± 1.99 | 550 ± 88 | 18.7 ± 6.2 | 10.9 ± 1.1 | 4.17 ± 2.77 | 376 ± 250 | 16.0 ± 5.3 | 3.33 ± 2.62 |
| Ovarian patient | 120 | 1.19 ± 0.24 | 0.615 ± 0.149 | 518 ± 60 | 39.8 ± 14.2 | 1.60 ± 0.26 | 0.520 ± 0.196 | 318 ± 97 | 35.7 ± 18.5 | 4.30 ± 0.54 |
| | 1,200 | 12.8 ± 3.41 | 5.13 ± 1.32 | 398 ± 21 | 25.9 ± 8.3 | 16.7 ± 2.9 | 4.20 ± 1.79 | 245 ± 99 | 19.8 ± 6.6 | 5.00 ± 2.93 |
| FaDu xenograft | 120 | 0.989 ± 0.228 | 3.88 ± 1.27 | 4359 ± 1230[a] | 71.0 ± 6.8[a] | 1.42 ± 0.18 | 3.84 ± 1.04 | 2660 ± 473[a] | 71.8 ± 1.7[a] | 6.42 ± 3.51 |
| | 1,200 | 12.2 ± 1.3 | 23.2 ± 5.4 | 1800 ± 300[a] | 58.6 ± 5.4[a] | 18.9 ± 5.5 | 17.7 ± 3.7 | 1010 ± 339[a] | 45.0 ± 5.8[a] | 4.05 ± 1.21 |

[a] $p < 0.05$, unpaired two-tailed Student's t-test.

Efflux of Paclitaxel from Histocultures

Figure 2:
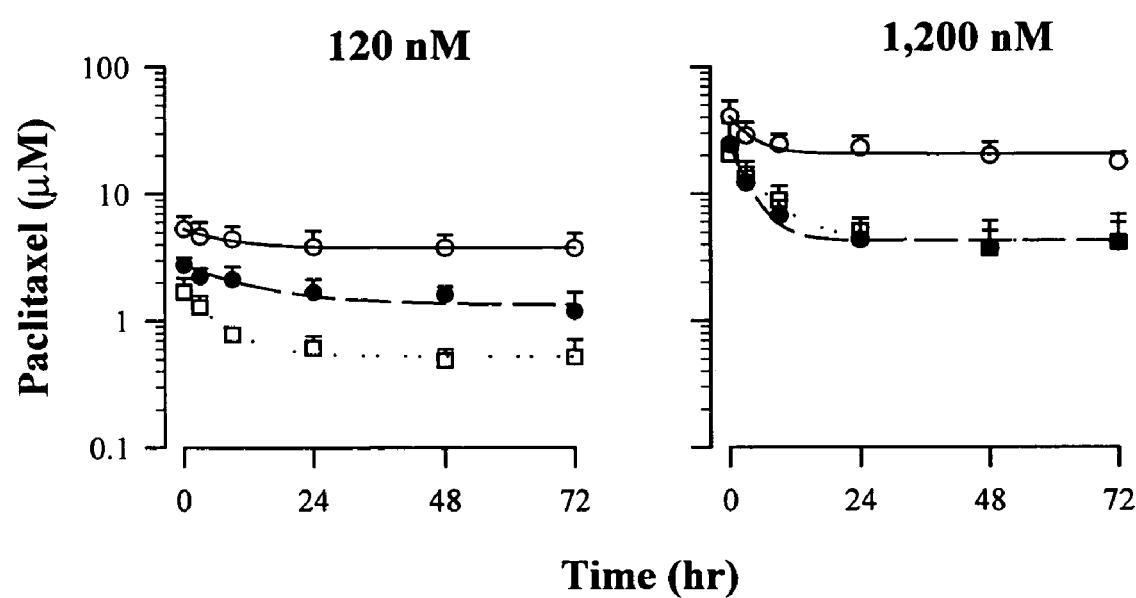
FIG. 2 is a line graph depicting the kinetics of paclitaxel efflux in patient and xenograft tumor histocultures. Patient head and neck tumors are represented by ●, patient ovarian tumors are represented by □, and FaDu xenograft tumors are represented by ○.

FIG. 2 and Table 2 compare the kinetics of drug efflux from patient and xenograft tumors. In all three tumor types, the drug concentration declined to a pseudo steady state level at 48 hr. The extent of efflux was also dependent on the initial concentration, ranging from 29% to 60% at 120 nM and from 41% to 81% at 1,200 nM in the first 24 hr. The decreases in drug concentration in the next 48 hr was several fold lower, ranging from 1% to 12% at 120 nM and from 3% to 13% at 1,200 nM. $T_{1/2,efflux}$, which is the time to reach 50% of the pseudo steady state level, ranged from 3 to 7.5 hr. The decreases in tumor concentrations were accompanied by increases in medium concentrations. The tumor-to-medium concentration ratios ranged from 400 to 4,000 at 24 hr and from 250 to 2,700 at 72 hr. These ratios exceed the steady state tumor-to-medium concentration ratios achieved during the uptake study (i.e. 20 to 120) by 8- to 38-fold, indicating that a sink condition was maintained during the efflux study. Hence, the high steady state tumor-to-medium concentration ratios indicate a significant retention of the drug in tumors, i.e. 19% to 71% of initial drug concentration was retained after 24 hr, and 16 to 72% retained after 72 hr. In general, the fractions retained and the tumor-to-medium concentration ratios attained at the lower initial medium concentration of 120 nM were significantly higher than those attained at the higher initial concentration of 1,200 nM (p<0.05, unpaired two-tailed Student's t-test). But the differences between the apparent $T_{1/2,efflux}$ at these two initial medium concentrations are not statistically significant. Collectively, these data indicate significant drug retention in tumors and that the extent of retention but not the rate of efflux is inversely related to drug concentration.

FIG. 2 and Table 2 show the results of an experiment designed to measure the paclitaxel efflux from histocultures of FaDu xenograft and patient tumors. Tumors were incubated with paclitaxel for 24 hr. After replacing the drug-containing medium with drug-free medium, the drug concentration remaining in histocultures at 24 and 72 hours post-treatment were analyzed to determine the time to reach 50% of the pseudo steady state level ($T_{1/2,efflux}$). The statis- Differences Between Patient and Xenograft Tumors.

Of the patient tumors the head and neck tumors show a trend of higher accumulation (i.e. high steady state tumor-to-medium concentration ratio) and a slower uptake rate (i.e. longer apparent $T_{1/2,uptake}$) compared to the ovarian tumors (Tables 1 and 2). However, the differences are not statistically significant, due to the large variability between individual tumors. In contrast, there are significant differences in the rate of drug uptake, extent of drug accumulation and extent of drug retention between patient tumors and the xenograft tumor (Tables 1 and 2). When compared to patient tumors, the xenograft tumor showed a slower uptake and a greater extent of accumulation when the initial drug concentrations were ≧120 nM, but not at the lower medium concentration of 12 nM. The xenograft tumor also showed a 3- to 4-times greater drug retention compared to patient tumors. The differences in the drug uptake and accumulation between patient and xenograft tumors were used to study the determinants of paclitaxel uptake and efflux in solid tumors.

Determinants of Paclitaxel Uptake and Efflux

The rate of paclitaxel uptake in tumors involves multiple kinetic processes; i.e. movement from media to collagen gel matrix, to tumor histocultures and then through interstitial space to cells, as well as binding to tubulins and microtubules and possibly other macromolecules (Jordan M A et al. (1993) *Proc Natl Acad Sci USA* 90:9552–9556; Manfredi J J et al. (1982) *J Cell Biol* 94:688–696). The binding to macromolecules determines the extent of drug accumulation; the plateau drug accumulation attained at higher drug concentration in culture medium reflects a saturation of binding sites (Jordan M A et al. (1996) *Cancer Res* 56:816–825; Kang et al. (1997) *Proc Am Assoc Cancer Res* 38:604). During efflux, the free drug including the drug dissociated from binding sites travels sequentially from intracellular space to interstitial space by diffusion and/or transport by the drug efflux mdr1 p-glycoprotein, to collagen gel matrix and to surrounding culture medium. Drug retention in tumors is determined by its binding to macromolecules and the rate of efflux is determined by the dissociation of drug from binding sites. The pseudo steady state attained during efflux reflects a slow dissociation of paclitaxel from binding sites.

Three studies were performed to identify the key determinants of paclitaxel uptake and efflux from solid tumors. These studies include (a) evaluation of drug diffusion from culture medium to histocultures, (b) evaluation of the role of the drug efflux mdr1 p-glycoprotein, and (c) evaluation of the role of cellularity and apoptosis.

Diffusion of Paclitaxel from Culture Medium to 3-Dimensional Tumor Histocultures This study determined the rate of drug diffusion from culture medium into the collagen gel matrix supporting the histocultures, to evaluate whether slow drug diffusion contributed to the slow drug penetration into solid tumors. One cm$^2$ collagen gel pieces were presoaked and placed in a well of a 6-well plate, containing 4 ml of complete culture medium. No tumors were added. After incubation for 3 to 4 days, the medium was replaced with 4 ml of 120 nM [$^3$H]paclitaxel-containing medium and incubated at 37° C. for 24 hr. At predetermined times, 100:1 of medium was removed from each well. For the sampling of medium trapped in the porous collagen gels, one piece of collagen gel was transferred to: a new plate and the medium was obtained by squeezing the gel with a pair of forceps. These procedures required less than 20 sec. The radioactivity in medium was determined. The results show that immediately (i.e., <12 min) after adding drug solution to the medium, the drug concentration in the culture, medium trapped in the collagen gel matrix ($C_{gel}$) was about 50% of the initial drug concentration in the culture medium. The more rapid increase in $C_{gel}$ compared to the increase in drug concentration in the histocultures suggests that drug diffusion from the medium through the collagen gel matrix is not the rate-limiting factor for the slow drug penetration into tumor histocultures in the first 24 hours.

Effect of Expression of the mdr1 p-Glycoprotein (Pgp) on Drug Accumulation in Patient and Xenograft Tumors.

The difference in Pgp expression in tumors was a factor that was considered in relation to the differential drug accumulation. The expression of Pgp was measured by immunohistochemical methods, using procedures described previously (Toth K et al. (1994) *Am J Pathol* 144:227–236). Briefly, tissue sections were de-waxed and rehydrated sequentially in xylene, ethanol and water. Tissue sections were boiled in a 0.1 M citrate buffer, pH 6.0, in a microwave oven, then cooled and washed in phosphate-buffered saline (PBS). The tissue sections were incubated with Dako blocking solution for 10 min and subsequently with the following antibody solutions for 2 hr: a mouse anti-human Pgp antibody (JSB-1, 1:200 dilution) and a rabbit antihuman Pgp polyclonal antibody (ab-1, 1:100 dilution). JSB-1 does not cross-react with MDR3 (Schinkel A H et al. (1991) *Cancer Res* 51:2628–2635). The incubation was carried out in a humidified chamber at room temperature. The antibodies were diluted in PBS containing 5 mg/ml bovine serum albumin. For negative controls, we used mouse IgG as the primary antibody. For positive controls, we used human adrenal gland which shows high Pgp expression (Pavelic Z P et al. (1993) *Arch Otolaryngol Head Neck Surg* 119: 753–757). After washing with PBS, the tissue sections were covered with the linker solution, and then with peroxidase-conjugated streptavidin solution. After washing twice with PBS, tissue sections were incubated for 5 to 7 minutes with diaminobenzidine and counterstained with hematoxylin.

Only tumors that were stained by two Pgp antibodies and showed Pgp proteins in at least two-third of the histocultures were considered Pgp-positive. By these criteria, the xenograft tumor, three head and neck tumors, and two ovarian tumors were Pgp-positive, whereas four head and neck tumors and one ovarian tumor were Pgp-negative. The accumulation of paclitaxel in these tumors was compared, at two initial medium concentrations of 120 and 12,000 nM. The results are shown in Table 3. The statistical significance of the differences between groups was analyzed by the two-tailed unpaired Student's t-test. Groups with statistically significant differences are also noted in Table 3.

TABLE 3

| | | Tumor-to-medium concentration ratio | | | | | |
|---|---|---|---|---|---|---|---|
| | Pgp | 120 nM | | 12,000 nM | | | |
| Tumor | status | n | 24 h | n | 24 h | 48 h | 72 h | 96 h |
| FaDu | + | 3 | 53 ± 10 | 3 | 29 ± 3 | 46 ± 6 | 51 ± 1 | 50 ± 8 |
| Patient | + | 3 | 30 ± 11$^a$ | 5 | 21 ± 5$^a$ | 26 ± 3$^a$ | 24 ± 1$^a$ | 25 ± 4$^a$ |
| Patient | − | 3 | 38 ± 3 | 5 | 31 ± 11 | 32 ± 9 | 33 ± 8$^b$ | 31 ± 10$^b$ |

$^a$Comparison between FaDu xenograft and Pgp-positive patient tumors, p < 0.05.
$^b$Comparison between FaDu xenograft and Pgp-negative patient tumors, p < 0.05.

The xenograft tumor showed a higher accumulation than the Pgp-positive patient tumors. Within the patient tumors, Pgp expression did not always result in a lower drug accumulation. For example, while the Pgp-positive patient tumors showed a trend of lower drug accumulation compared to the Pgp-negative patient tumors at the higher drug concentration of 12,000 nM, the difference was small (i.e. average of <25%) and not statistically significant. Furthermore, no difference between the two groups was observed at the lower drug concentration of 120 nM. These data indicate that Pgp expression, while it might have contributed to the lower drug accumulation in some tumors, is not the major determinant of drug accumulation and did not fully account for the 50 to 100% difference in drug accumulation between patient and xenograft tumors.

Role of Cellularity and Apoptosis in Paclitaxel Penetration, Accumulation and Retention in Histocultures The rate of [$^3$H]paclitaxel penetration in tumors and the spatial relationship between drug penetration, tumor architecture and tumor cell distribution were evaluated using autoradiographic techniques and image analysis. The autoradiographic method was as described previously (Lesser G J et al. (1995) *Cancer Chemother Pharmacol* 37:173–178). After incubation with [$^3$H]paclitaxel (0.231 and 2.31 μCi/ml, corresponding to 12 and 120 nM) for 1 hour to 3 days, tumor histocultures were collected and washed two times by dipping in ice-cold drug-free medium. Tissue samples were mounted on cryostat chucks with embedding matrix (O.C.T. Compound, Miles Inc., Ellchart, Ind.) and cut into 10 μm thick sections in a cryostat at −20° C. Sections were thaw-mounted on a glass slide and heat-fixed on a slide warmer for 15 min. The slides containing the tissue sections were placed against tritium-sensitive film (Ultrofilm) in an X-ray cassette and exposed for one to two weeks at room temperature. The films were developed for 3–5 minutes at room temperature (D-19 Developer), placed in a stop bath for 30 seconds, immersed in fixer for 3 minutes and exposed to running room temperature water for 15 minutes. The films were then rinsed in Photo-flo 200 and allowed to air-dry. Separately, the tissue section slides were stained with hematoxylin and eosin.

Image analysis was then used to capture the autoradiographic image (where the grains indicated the location of the radiolabeled drug) and the histologic image of the tissue section slide stained with hematoxylin and eosin (which showed the tissue structure and distribution of tumor cells). The threshold for the autoradiographic image was adjusted to minimize the background signal. The autoradiographic image was overlaid on the histologic image to visualize the distribution of [$^3$H]paclitaxel in tumor histocultures.

Head and neck tumors and a xenograft tumor were treated with 120 nM paclitaxel. The drug uptake rate in the xenograft tumor was about 50 to 80% slower than in patient tumors and the accumulation was twice that in patient tumors (Table 1). In the xenograft tumor, paclitaxel penetrated only a few cell layers in the periphery after 4 hours, 10 to 15 cell layers after 24 hours, and became evenly distributed throughout the tumor (>80 cell layer thick) at and after 48 hours. These data indicate an abrupt increase in the drug penetration rate after 24 hours. The drug penetration in the patient tumor was more rapid, reaching about one-half of the tumor histoculture at 4 hours and becoming evenly distributed at 24 hours. In both xenograft and patient tumors a comparison of the radioactivity in areas with high and low cell density indicates a higher localization of radioactivity in cells compared to interstitial space. In addition, the rapid distribution of radioactivity to the areas with a low epithelial-cell density at earlier time points, together with the observation of a more rapid drug penetration in patient head and neck tumors which has a lower tumor cell fraction, (i.e., 51±18% of the histocultures was represented by tumor cells) as compared to the FaDu xenograft tumor which has a higher tumor cell fraction (i.e., 79±7.0% of the histocultures was represented by tumor cells), suggest that reduced cellularity corresponds to a more rapid drug penetration.

The above observations suggest that drug penetration may be enhanced by a loss of cellularity, e.g. following apoptosis induced by paclitaxel treatment which occurs after a 16 to 24 hour delay (Saunders D E et al. (1997) *Int J Cancer* 70:214–220). This hypothesis was confirmed by evaluating the changes in tissue composition with time, for the xenograft tumor. The xenograft tumor was treated with two concentrations of paclitaxel, i.e. 120 nM which caused significant apoptosis and 12 nM which did not cause significant apoptosis. The fractions of stromal tissue and tumor cells in each histoculture were measured using image analysis. Briefly, stromal and tumor cells of a 100× magnification field were outlined with the computer mouse. The sizes of each of these regions were determined via image analysis by counting the number of pixels in the region. To determine the fraction of apoptotic cells in a tumor, the tumor cell density and the fraction of apoptotic cells were determined by counting the number of total tumor cells and apoptotic cells in nonnecrotic regions at 400× magnification (3 microscopic fields/tumor). Apoptotic cells were determined based on morphological changes in tumor cells such as chromatin condensation and margination, disappearance of nucleoli, formation of membrane blebs, apoptotic bodies and/or cell shrinkage (Kerr J F R et al. (1994) *Cancer* 73:2013). This method has been shown to yield the same results as the terminal deoxynucleotidyl transferase-mediated dUTP nick end labeling (TUNEL) method (Gan Y et al. (1996) *Cancer Res* 56:2086; Gold R et al. (1994) *Lab Invest* 71:219–225). For each tumor piece, 50 to 100 images were processed, and the fractions of the tumor represented by tumor cells, stromal tissue, and interstitial space were calculated.

When xenograft tumor histocultures were treated with 120 nM paclitaxel, there was a significant reduction in tumor cell density and increase in apoptotic cells. This effect was first detected at 24 hours and progressively increasing with time. The fraction of apoptotic cells in the treated tumors was ~30% at 24 hours and increased to ~50% at 72 hours, whereas the untreated controls showed a <5% apoptotic cells. The onset of apoptosis and expansion of interstitial space at 24 hours coincided with the abrupt increase in drug penetration, i.e. the drug penetrated >80 cell layers during the second 24 hours opposed to 15 cell layers during the first 24 hours. When tumors were treated with 12 nM paclitaxel, it did not produce significant reduction in cellularity nor increase in apoptotic cells; the fraction of apoptotic cells remained relatively constant at ≧7%. Under these conditions, drug penetration was restricted to the periphery. These results indicate that the drug-induced apoptosis causes a reduction in tumor cell density and thereby enhances drug penetration into the inner layers of the solid tumor.

Summary

In summary, this example shows that (a) the penetration of paclitaxel in tumors is more rapid but the accumulation is lower as the density of epithelial tumor cells decreases, (b) drug-induced apoptosis enhances drug penetration into the inner cell layers of solid tumors, (c) the concentration-dependent drug penetration rate is related to the concentration-dependent apoptotic effect, and (d) the time-dependent drug penetration is related to the kinetics of apoptosis.

Example 2

Effect of Apoptosis-Inducing Pretreatment on Drug Penetration and Accumulation in Tissues Using Paclitaxel as the Apoptosis Inducing Agent This example consists of in vitro and in vivo studies. The in vitro study was performed using the human pharynx FaDu xenograft tumor maintained in athymic mice. The in vivo study was performed using a syngeneic animal tumor, i.e., the MAT-LyLu prostate tumor maintained in Copenhagen rats.

Drug Treatment—In Vitro Studies

Drug treatment was as previously described. The histocultures were transferred to a collagen gel presoaked with drug-containing medium for at least 8 hr. The latter was to ascertain that the drug concentration in the medium inside the collagen gel was at equilibrium with the surrounding medium, in order to eliminate the delay in drug transport from medium through the collage gel. Drug treatment was terminated by transferring histocultures to a collagen gel presoaked with drug-free medium. Histocultures were transferred using a pair of hooked forceps and care was exercised to avoid squeezing or pinching.

Effect of Apoptosis-Inducing Pretreatment on Drug Deliver in Tumor—In Vitro Studies.

The spatial distribution of [$^3$H]paclitaxel in histocultures was studied using autoradiography and imaging techniques as described in Example 1. The total drug concentration in tumor histocultures was measured as described in Example 1. Briefly, after incubating with 4 ml of culture medium containing a mixture of radiolabeled and nonradiolabeled paclitaxel (specific activity, 0.301:Ci/ml), histocultures were harvested and analyzed for total radioactivity using liquid scintillation counter. Thirty to 35 tumor histocultures were used for each time point.

Two studies were performed. In the first study, two groups of histocultures were incubated with the same concentration of [$^3$H]paclitaxel, 10 or 50 nM for 72 hr. These two groups received identical total exposure to radiolabeled paclitaxel, except the pretreated group also received an additional exposure of 3000 nM hr nonradiolabeled paclitaxel (i.e., 1,000 nM of nonradiolabeled paclitaxel for 3 hr), initiated at 24 hr prior to the radiolabeled dose. The drug concentration and the timing of the pretreatment was found in a preliminary study to cause significant apoptosis (~30%) at 24 hr. The second study used the same total drug exposure, i.e., 1,200 nM hr, but by different schedules as described below. For both studies, histocultures were collected at predetermined intervals after [$^3$H]paclitaxel treatment, and analyzed for drug penetration. The first study was used to demonstrate qualitatively the effect of pretreatment on the rate of drug penetration in solid tumor. Drug accumulation was evaluated only in the second study, because in the first study, the dilution of [$^3$H]paclitaxel by nonradiolabeled drug was expected to alter the specific activity of [$^3$H]paclitaxel and, therefore, affect data accuracy.

The results shows the effect of pretreatment with 1:M nonradiolabeled paclitaxel on [$^3$H]paclitaxel penetration in FaDu tumor histocultures. The nonradiolabeled paclitaxel was not detected by autoradiography and did not interfere with the detection of [$^3$H]paclitaxel. The example used two concentrations of [$^3$H]paclitaxel that differed in their ability in inducing apoptosis and reducing tumor cell density, with the 50 nM concentration being more effective than the 10 nM concentration (Table 4). Without the pretreatment, tumor penetration of [$^3$H]paclitaxel at 10 nM was limited to the periphery of the histocultures throughout 72 hr, whereas penetration at 50 nM concentration in the first 24 hr was limited to the periphery but subsequently increased, along with increased apoptotic fraction and reduced-cell density, such that drug distributed evenly throughout the tumor by 72 hr. The paclitaxel pretreatment induced apoptosis and reduced the cell density by the time the [$^3$H]paclitaxel treatment was applied. The pretreatment enhanced the penetration of [$^3$H]paclitaxel at both 10 and 50 nM concentrations such that even distribution in tumor was attained at 72 and 24 hr, respectively. These findings suggest that the fractionated doses separated by an interval that allows for apoptosis to occur would have result in greater drug penetration and accumulation than a continuous treatment schedule of the same total drug exposure (i.e., product of concentration and time, C×T).

Table 4 shows the results of an experiment where tumor histocultures were treated with different concentration of [$^3$H]paclitaxel with or without pretreatment by 1:M nonradiolabeled paclitaxel. The fraction of apoptotic cells and the tumor cell density were determined by counting the number of total and apoptotic tumor cells in 400× microscopic fields (3 fields per tumor).

TABLE 4

| Drug concentration and treatment duration | Apoptotic fraction, % | | Cell density | |
|---|---|---|---|---|
| | Without pretreatment | With Pretreatment | Without pretreatment | With Pretreatment |
| 10 nM | | | | |
| 4 hr | 3.93 ± 0.87 | 23.6 ± 1.3 | 86.3 ± 4.0 | 64.2 ± 3.5 |
| 16 hr | 4.98 ± 0.84 | 24.6 ± 4.8 | 80.2 ± 2.9 | 64.3 ± 1.8 |
| 24 hr | 7.32 ± 1.80 | 26.6 ± 2.4 | 81.6 ± 2.5 | 64.0 ± 5.2 |
| 32 hr | 6.64 ± 1.07 | 30.1 ± 3.4 | 79.9 ± 2.1 | 60.1 ± 4.2 |
| 48 hr | 9.18 ± 1.31 | 34.9 ± 5.2 | 77.8 ± 3.0 | 62.3 ± 3.1 |
| 72 hr | 11.0 ± 1.7 | 31.0 ± 4.4 | 82.6 ± 2.2 | 61.0 ± 2.2 |
| 50 nM | | | | |
| 4 hr | 2.74 ± 0.12 | 26.3 ± 5.4 | 85.8 ± 3.6 | 63.1 ± 4.5 |
| 16 hr | 7.97 ± 2.03 | 36.0 ± 3.9 | 83.9 ± 3.3 | 60.8 ± 4.9 |
| 24 hr | 17.0 ± 2.8 | 36.4 ± 2.0 | 77.0 ± 3.8 | 58.3 ± 1.1 |
| 32 hr | 19.1 ± 2.5 | 37.4 ± 4.5 | 71.2 ± 4.6 | 53.2 ± 2.1 |
| 48 hr | 28.3 ± 2.9 | 39.8 ± 3.1 | 68.8 ± 2.5 | 53.6 ± 2.4 |
| 72 hr | 27.2 ± 3.0 | 37.9 ± 3.4 | 61.1 ± 2.8 | 47.8 ± 3.2 |

To evaluate the effect of treatment schedule on paclitaxel delivery in tumors, a second study examined the drug penetration and accumulation in two groups that were treated with the same C×T (i.e., 1,200 nM·hr), given by two schedules. The pretreatment group received fractionated doses, i.e., 600 nM [$^3$H]paclitaxel for 1 hr, followed by incubation in drug-free culture medium for additional 23 hr to allow apoptosis to occur, and then treated with 50 nM [3H]paclitaxel for 12 hr. The control group was incubated with 50 nM [3H]paclitaxel continuously for 24 hr. In the control group, paclitaxel penetration was restricted to the 5 to 10 cell layers in the periphery of the histocultures in the first 24 hr, at which time drug-induced apoptosis began to appear. While drug penetration increased simultaneously with an increase in apoptotic fraction and reduction in cell density during the next 12 hr, drug penetration remained confined to less than 20 cell layers in the periphery. In comparison, the pretreatment group showed a higher apoptotic fraction, a lower cell density, and a more rapid penetration, resulting in even drug distribution throughout histocultures at 36 hr (Table 5). A comparison of drug accumulation in the two groups showed a 40% higher drug accumulation in the pretreatment group at the end of drug treatment (i.e., at 36 hr in pretreatment group vs at 24 hr in control group; Table 5), in agreement with the more extensive drug penetration as shown by autoradiography. The results of this study confirm that a fractional treatment separated at an interval for drug-induces apoptosis and reduction in cell density will result in greater drug penetration and accumulation into tumors than a single continuous treatment.

Table 5, listed below, shows the result of the experiment, in which tumor histocultures were treated with equal C×T of [$^3$H]paclitaxel, i.e., 1,200 nM·hr, by two different schedules. One schedule used 50% of the total C×T to induce apoptosis, whereas the other schedule used continuous treatment. Concentrations of [$^3$H]paclitaxel in tumor histocultures were determined by liquid scintillation counting. The fraction of apoptotic cells and cell density were determined by counting the number of total and apoptotic tumor cells in 400× microscopic fields (3 fields per tumor).

TABLE 5

| Treatment Schedule | Time (hr) after initiation of treatment | Apoptotic fraction (%) | Cell density | Paclitaxel in tumor (:M) |
|---|---|---|---|---|
| 600 nM × 1 hr →23 hr later →50 nM × 12 hr | 24 | 20.3 ± 4.3 | 60.9 ± 1.3 | 2.68 ± 0.31 |
| | 36 | 25.4 ± 3.4 | 62.4 ± 4.2 | 4.33 ± 0.29 |
| 50 nM × 24 hr | 24 | 15.2 ± 3.34 | 71.3 ± 2.9 | 3.11 ± 0.31 |
| | 36 | 17.0 ± 3.94 | 72.6 ± 3.2 | 2.01 ± 0.32 |

Collectively, these results indicate that under in vitro conditions, (a) an apoptosis-inducing pretreatment enhanced the drug penetration during subsequent treatments, and (b) treatments at higher drug concentrations that induced appreciable apoptosis and reduced tumor cell density resulted in more rapid drug penetration compared to treatments at lower concentration.

Effect of Apoptosis-Inducing Pretreatment on Drug Accumulation in Tumors—In Vivo Studies The rat MAT-LyLu tumor cells were originally obtained from Dr. J. Isaacs (Johns Hopkins University, Baltimore, Md.), and has been maintained in RPMI-1640 medium supplemented with 9% heat-inactivated FBS, 2 mM L-glutamine, 90:g/ml gentamicin and 90:g/ml cefotaxime sodium. Tumor cells ($5 \times 10^6$ cells in 0.1 ml medium, >90% viability, as determined by trypan blue exclusion) were injected subcutaneously in the right and left upper backs of a male Copenhagen rat with a 21 G needle. Experiments were initiated when the tumor was between 0.3 to 0.5 g in size.

The jugular vein and carotid artery of tumor-bearing rats were catheterized, under light ether anesthesia, with polyethylene tubing (PE-50, Becton Dickinson Co., Sparks, Md.) for drug administration and for blood sampling, respectively. Each catheter was exteriorized to the dorsal side of the neck and attached to a second polyethylene tubing (PE-50), respectively. The catheters and tubings were covered with a metal coil tubing. Animals were allowed to recover for 4–5 hr, and then given an intravenous infusion of paclitaxel using an infusion pump (Harvard Apparatus, Southnatick, Mass.). Paclitaxel was dissolved in Cremophor EL/ethanol (1:1, v/v) and diluted with 0.9% NaCl. The total infusion volume was 2 to 3 ml and the final Cremophor EL concentration in dosing solution was 10 to 15%. Five groups of animals were treated as described in the Results. Blood samples (0.12 or 0.22 ml) were obtained at predetermined times. Plasma fraction was obtained by centrifugation at 2,000 g for 3 min, and stored at −70° C. for HPLC analysis. At the end of the experiment, tumors were harvested. One quarter of a tumor was fixed in 10% neutralized formalin solution and processed for tissue morphology evaluation. Tumor cell density and the fraction of apoptotic cells were determined by counting the number of tumor cells and apoptotic cells in nonnecrotic regions at 400× magnification (5 microscopic fields/tumor). The remainder of the tumor was stored at #70° C. until HPLC analysis for drug concentration.

The concentration of nonradiolabeled paclitaxel in plasma and tumor was analyzed by our previously reported HPLC assay using a column switching method (Song D et al. (1995) *J Chromatogr B Biomed Appl.* 663:337). Preweighed tumors were homogenized, mixed with the internal standard, 100:1 cephalomanine (10:g/ml in methanol). The HPLC stationary phase consisted of a cleaning column (NovaPak $C_8$, 75×3.9 mm ID, 4:m particle size, Waters Associates, Milford, Mass.) and an analytical column (Bakerbond Octadecyl, 250×4.6 mm ID, 5:m particle size, J. T. Baker, Phillipsburg, N.J.). Samples were injected onto the clean-up column and eluted with the clean-up mobile phase (37.5% acetonitrile in Water) at 1 ml/min. Concurrently, the analytical mobile phase (49% acetonitrile in Water) was directed through the analytical column at a flow rate of 1.2 ml/min. The fraction from 5 to 12 min containing paclitaxel and cephalomanine was transferred from the clean-up column onto the analytical column. Detection of paclitaxel and cephalomanine was at 229 nm, with a detection limit of 1 ng paclitaxel per injection.

Pharmacokinetic and tissue morphology studies were conducted to identify potential doses and times for administration of the drugs. The results, listed in Table 6, show that a pretreatment dose of 5 mg/kg infused over 1 hour is sufficient to induce apoptosis and reduce tumor cell density. These changes in tissue composition, as shown in the in vitro studies described above, are sufficient to enhance drug penetration in tumors. The pharmacokinetic data further showed a major half-life of 1.1 hour for paclitaxel in rats, indicating that drug concentration in plasma and tumor will be, theoretically, within 97% of a steady state following an infusion of six hours or longer (i.e., $\geq$5 half-lives). The latter is confirmed by the plasma concentration-time profiles showing that the concentrations approached plateau values at the end of 6 and 12 hr infusions (13% difference).

Table 6 shows the results of an experiment where animals received the indicated treatment (Tx). Concentrations of paclitaxel in tumors and plasma were determined by HPLC. Fraction of apoptotic cells and cell density were determined by counting the number of total and apoptotic cells in 400× microscopic fields (5 fields per tumor). Mean±SD.

TABLE 6

| Group | Infusion rate (mg/kg/hr) & schedule | Total dose (mg/kg) | N | Tumor conc. (:g/g) at specified time | Plasma conc. At end of Tx (:g/ml) | Tumor-to-plasma conc. ratio at end of Tx | Apoptotic fraction, % | Cell density |
|---|---|---|---|---|---|---|---|---|
| 1 | 5 × 1 hr → 0.83 × 6 hr at 24 hr | 10 | 5 | 3.94 ± 0.35 at 30 hr[a] | 1.42 ± 0.11 | 2.80 ± 0.28[a] | 14.5 ± 2.5[b] | 83 ± 4.69[b] |
| 2A | 5 × 1 hr at 0 hr | 5 | 4 | 2.76 ± 0.57 at 1 hr | 6.01 ± 0.64 | 0.46 ± 0.09 | 1.5 ± 0.9 | 120 ± 4.35 at 1 hr |
| 2B | 5 × 1 hr at 0 hr | 5 | 4 | <0.35 at 24 hr | ND | NA | 11.2 ± 2.3[c] | 85 ± 4.52 at 24 hr[c] |

TABLE 6-continued

| Group | Infusion rate (mg/kg/hr) & schedule | Total dose (mg/kg) | N | Tumor conc. (:g/g) at specified time | Plasma conc. At end of Tx (:g/ml) | Tumor-to-plasma conc. ratio at end of Tx | Apoptotic fraction, % | Cell density |
|---|---|---|---|---|---|---|---|---|
| 3 | 0.83 × 6 hr at 0 hr | 5 | 4 | 2.26 ± 0.13 at 6 hr | 1.31 ± 0.12 | 1.73 ± 0.18 | 3.5 ± 1.5 | 112 ± 6.08 |
| 4 | 5 × 1 hr at 0 hr + 0.83 × 6 hr at 1.2 hr | 10 | 4 | 3.24 ± 0.31 at 7.2 hr | 2.98 ± 0.60 | 1.20 ± 0.30 | 5.8 ± 2.2 | 108 ± 5.78 |
| 5 | 0.83 × 12 hr | 10 | 5 | 2.95 ± 0.34 at 12 hr | 1.50 ± 0.06 | 1.98 ± 0.23 | 6.5 ± 1.6 | 115 ± 5.18 |

[a] $p < 0.05$, compared to all other groups.
[b] $p < 0.01$, compared to all other groups except Group 2B.
[c] $p < 0.01$, compared to all other groups except Group 1.

Three in vivo studies were performed. The first study examined the effect of pretreatment on drug delivery to tumor tissue, in three groups of animals. Group 1 received a pretreatment of 5 mg/kg over 1 hour and, at 24 hours, a second dose infused at a slower rate (i.e., 5 mg/kg over 6 hours). To obtain the baseline measurements of drug delivery to tumor at each of the two doses, Group 2 received only the pretreatment, and Group 3 received only the second treatment. In the absence of enhanced drug delivery due to apoptosis, the drug concentration in Group 1 should be lower than the sum of the concentrations in Groups 2 and 3, because the concentration derived from the pretreatment dose in Group 1 was measured at the end of the 30 hr total treatment time which, due to the continuing decline with time, should be lower than the concentration in Group 2 which was measured immediately after the 1 hr pretreatment. Conversely, in the presence of a substantially enhanced drug delivery due to apoptosis, the concentration in Group 1 may exceed the sum of concentrations in Groups 2 and 3. The results show a 50% higher tumor concentration in Group 1 at 30 hr or at the end of treatment compared with the sum of the concentration derived from Group 2 at 24 hr plus the concentration derived from Group 3 at 6 hr (Table 6), thus supporting our hypothesis of enhanced drug delivery due to apoptosis induced by the pretreatment.

The second study compared the tissue morphology and tumor concentration in Group 1 with those in Group 4 which received the same two doses by the same infusion schedules as Group 1, with the exception that the two doses were separated by only 10 min (time required to change and reset the infusion syringe and pump) as opposed to the 23 hr in Group 1. As shown above, 24 hr was the duration needed for apoptosis and reduction in cell density to occur. At the end of treatment (30 hr for Group 1 and 7.2 hr for Group 4), Group 4 showed a 60% lower apoptosis, 30% higher cell density and 18% lower drug concentration, compared to Group 1 (Table 6). These results indicate the importance of timing on drug-induced changes in tissue morphology and on drug delivery.

The third study compared the tissue morphology and tumor concentration in Group 1 to those in Group 5 which received the same total dose as Group 1 with the exception that the dose was delivered at a slower rate continuously over a longer duration, i.e., 12 hr. At the end of treatment (30 hr for Group 1 and 12 hr for Group 5), Group 5 showed a 35% lower apoptosis and 25% higher cell compared to Group 1, and the drug concentration at 12 hr in Group 5 was 25% lower than the concentration at 30 hr in Group 1 (Table 6).

Another measurement of drug penetration in tumor is the tumor-to-plasma concentration ratio at the end of drug treatment when the plasma concentration in Groups 1, 4 and 5 were at an apparent steady state. A comparison of the tumor-to-plasma concentration ratio in these three groups shows a 130% and 40% higher ratios in Group 1 compared to Groups 4 and 5, respectively (Table 6), confirming the higher drug delivery in the group receiving the apoptosis-inducing pretreatment.

Collectively, the results of the in vivo studies confirm the findings in tumor histocultures, and further suggest a requirement of >10% apoptosis and >25% reduced cell density for enhancing drug delivery to tumor under in vivo conditions.

Example 3

Effect of Apoptosis-Inducing Pretreatment on Drug Penetration and Accumulation in Tissues Using Doxorubicin as the Apoptosis Inducing Agent In this example, the penetration of doxorubicin into multilayer tissue was monitored using prostate tumor specimens obtained from human cancer patients and using the human prostate PC3 xenograft tumor maintained in athymic mice. Doxorubicin was monitored by fluorescence.

Accumulation of Doxorubicin in Tumor Histocultures

Histocultures of tumors were incubated with 1, 5 or 20:M doxorubicin as described in Example 1. These concentrations were chosen based on the previously published data which demonstrate that 0.4:M doxorubicin was sufficient to produce, in patient prostate tumors, a 90% inhibition of tumor cell proliferation, and that 2.1:M and 4.2:M doxorubicin were sufficient to produce 50 and 90% cell death, respectively (Chen et al., (1998) Clin. Cancer Res. 4:277–282, 1998). At 4, 12, 24, 36, 48, and 72 hours, histocultures were collected and processed as described in Example 1. The fluorescence emitted by doxorubicin was visualized using fluorescence microscopy. The excitation and emission wavelengths were 546 nm and 565 nm, respectively. Microscopic images were captured using a Charged Couple Device (CCD) camera and the captured images were analyzed using Optimas image analysis software (Silver spring, MD). The doxorubicin concentration in tissues was quantified using standard curves (each curve contained six data points), established as follows. Samples for the standard curves were prepared by applying known amounts of doxorubicin in solution to microscope sections of blank dog prostate tissue. The standard doxorubicin solutions (2:1) were pipetted on 10:m-thick blank tissue sections, and carefully spread over a surface area of approximately 1.5–2 cm$^2$. The standard slides were scanned using the same conditions as the samples. The average fluorescence intensity per area were measured. Plots of the fluorescence readings against the applied doxorubicin concentrations in the standard curve samples provided the standard curves used to quantify the doxorubicin in the actual samples. For the latter, at least three sections were used to obtain the mean value in one tumor, and at least three tumors were used to obtain the mean value at each time point.

Figure 3:
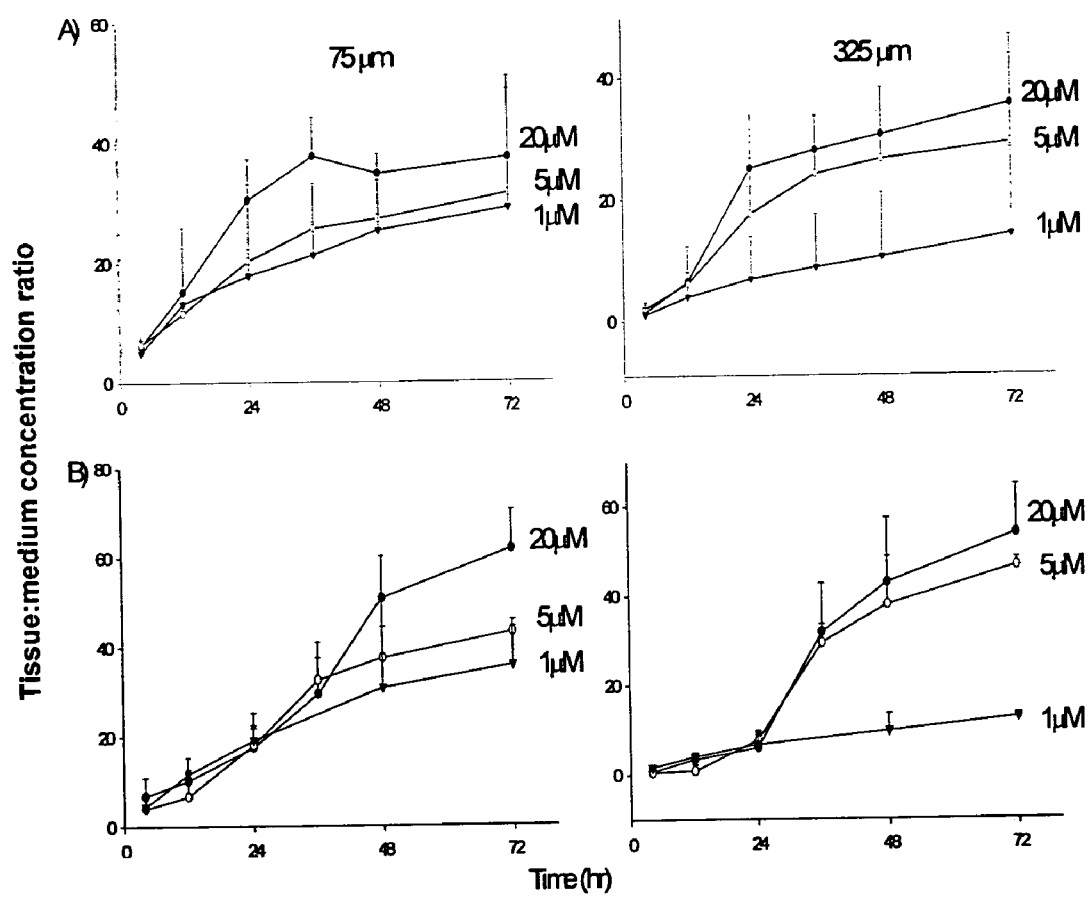
FIG. 3 is a graph depicting the accumulation of doxorubicin in tumor tissues, expressed as tissue-to-medium concentration ratio, as a function of time and initial extracellular drug concentrations. The average drug concentration in the periphery of tumor (i.e., 75 μM) and in the far end of the tumor (i.e., 325 μM from the periphery of the tumor in contact with the culture medium) are shown. (A) Top panels: patient prostate tumors. (B) Bottom panels: PC3 xenograft tumors. Tumors treated with 1 μM doxorubicin are represented by ▼. Tumors treated with 5 μM doxorubicin are represented by ○. Tumors treated with 20 μM doxorubicin are represented by ●.

FIG. 3 summarizes the accumulation of doxorubicin in tumor tissues, expressed as tissue-to-medium concentration ratio, as a function of time and initial extracellular drug concentrations. The results show that drug concentration in the periphery of tumor (i.e., 75 μm) and in the far end of the tumor (i.e., 325 μm from the periphery of the tumor in contact with the culture medium) rose more rapidly in patient tumors than in the PC3 xenograft tumor. The ratios reached at 72 hr increased with the extracellular drug concentrations, but the increase was not linear with concentration. The latter may be due to the nonlinear drug binding which became saturated at the higher drug concentration, as described for paclitaxel in Example 1. At the lower drug concentration of 1 μM, the drug concentration in the far end of the tumor remained several fold-lower compared to the concentration in the periphery. In contrast, at the higher drug concentrations of 5 and 20 μM, the drug concentrations in the far end of the tumors approached the concentrations in the periphery of the tumors. Collectively, these data indicate that the rate and extent of drug accumulation in solid tumors are dependent on time and initial drug concentration.

Table 7 shows the results of doxorubicin accumulation in patient tumors and the PC3 xenograft tumor, after 72 hr incubation with doxorubicin at 1, 5 and 20 μM.

tumor, compared to patient tumors, is due to the higher tumor cell density in the xenograft tumor.

Rate of Doxorubicin Penetration into Tumors

The rate of doxorubicin penetration into patient and PC3 xenograft tumors was monitored using fluorescence microscopy. The presence of fluorescence corresponds to the presence of doxorubicin and, hence, indicates the spatial distribution of doxorubicin in tumor tissue. The findings on doxorubicin penetration and distribution in tumor tissues are similar to the findings on paclitaxel as described in Example 1. For example, the patient and xenograft tumors show different rate and pattern of doxorubicin penetration, and the rate of drug penetration was also dependent on the drug concentration. For the patient tumors treated with 5 or 20 μM, the fluorescence signal was confined to the periphery (about 75 μm thick) during the first 12 hr, but became evenly distributed throughout the histoculture (about 325 μm thick) after 24 hr. For the xenograft tumor treated with the same drug concentrations (i.e., 5 or 20 μM), the fluorescence signal was confined to the periphery during the first 24 hr, and became evenly distributed only after 36 hr. At the lower drug concentration of 1 μM, the drug was distributed evenly throughout the patient tumors by 72 hr but remained confined to the periphery of the xenograft tumor at 72 hr.

Figure 4:
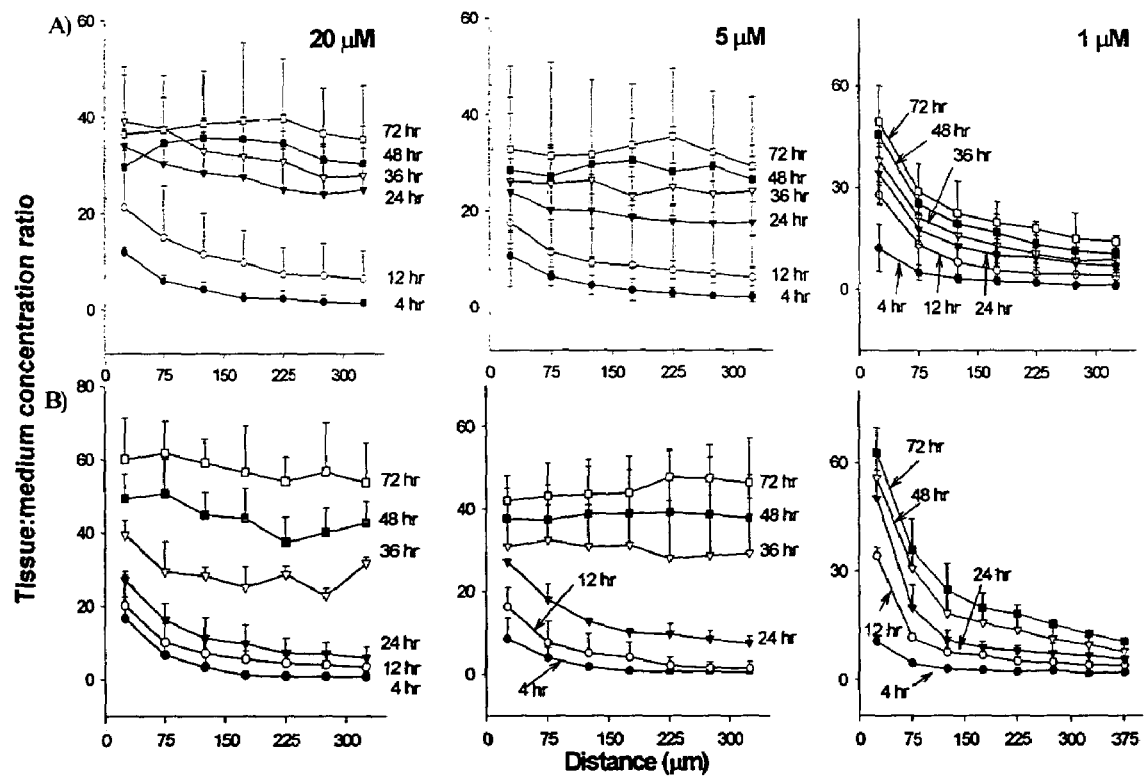
FIG. 4 is a graph depicting the doxorubicin concentration in tumor tissue, expressed as tissue-to-medium concentration ratio, as a function of the distance from the edge of the tumor in contact with the culture medium. (A) Top panels: patient prostate tumors. (B) Bottom panels: PC3 xenograft tumors. Tumors were treated with 1 (right panels), 5 (middle panels) and 20 (left panels):M doxorubicin. The treatment times are directed noted on the graph.

FIG. 4 summarizes the drug concentration in tumor tissue, expressed as tissue-to-medium concentration ratio, as a function of the distance from the periphery of the tumor histocultures. The results show that the attainment of an equilibrium between the drug-concentration in the far end of the tumor (i.e., 325 μm from the periphery of the tumor in contact with the culture medium) with the drug concentration in the periphery of the tumor (i.e., 75 μm) depends on the initial drug concentration in the culture medium. At the lower drug concentration of 1 μM, the drug concentration in the far end of the tumor did not reach equilibrium with the

TABLE 7

| Tumor | Drug concentration in culture medium, μM | Tissue concentration at 72 hr | Tissue-to-medium concentration ratio at 72 hr | PC3 xenograft-to-patient tumor concentration ratio at 72 hr | Cell density in untreated tumor (cells per mm$^2$) |
|---|---|---|---|---|---|
| Patient tumors | 1 | 29.2 ± 7.8 | 29.2 ± 7.8 | 1.15 | 1864 ± 25* |
|  | 5 | 158 ± 70.9 | 31.6 ± 14.2 | 1.35 |  |
|  | 20 | 739 ± 531 | 36.9 ± 26.5 | 1.5 |  |
| PC3 xenograft tumor | 1 | 33.6 ± 3.9 | 33.6 ± 3.9 | Not applicable | 2418 ± 66* |
|  | 5 | 213 ± 16.4 | 42.7 ± 3.3 |  |  |
|  | 20 | 1107 ± 193 | 55.3 ± 9.6 |  |  |

*p < 0.05, unpaired two-tailed Student's t-test.

Doxorubicin concentration in both patient tumors and the PC3 xenograft tumor increased with incubation time and with the initial drug concentration in the culture medium. The findings on the rate and extent of doxorubicin accumulation in patient and xenograft tumors are similar to the findings on paclitaxel described in Example 1. For example, drug accumulation in the xenograft tumor is slower compared to patient tumors (FIG. 3). Drug concentration in the xenograft tumor shows a higher tumor-to-medium concentration ratio compared to patient tumors, although the difference is not statistically significant (FIG. 3 & Table 7). The tumor cell density in the xenograft tumor without drug treatment is 1.3 fold-higher compared to patient tumors. Collectively, these data indicate that the slower drug uptake rate and the higher drug accumulation in the PC3 xenograft concentration the periphery. For the higher concentrations of 5 and 20 μM, the equilibrium was attained at 36 hr.

Collectively, these results indicate that rate and extent of doxorubicin penetration into tumor is dependent on the treatment time and the extracellular drug concentration. These data are similar to the findings for paclitaxel, as described in Example 1, and suggest that doxorubicin-induced apoptosis enhances the rate and extent of drug penetration into tumors.

Roles of Cell Death in Drug Penetration

Figure 5:
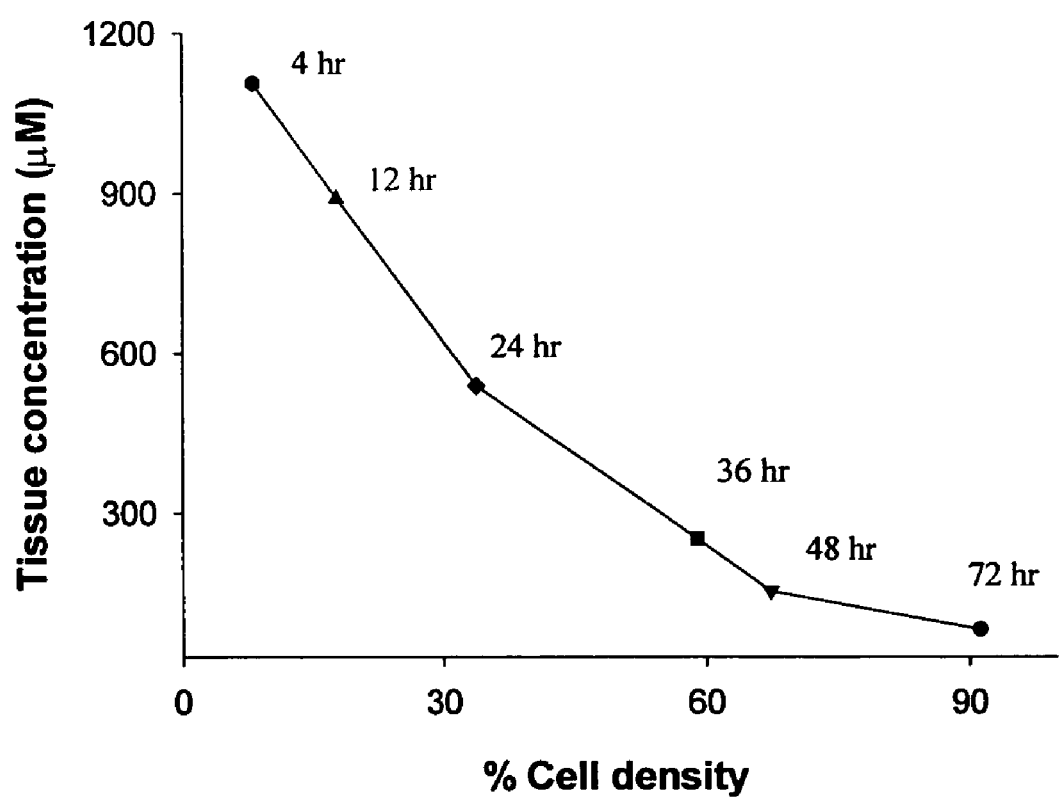
FIG. 5 is a graph depicting the effect of cell density in the periphery of the tumor (i.e., 100 μm distance from the edge in contact with the culture medium). Percent cell density is the ratio between the cell density in the treated tumors and the cell density in the untreated control samples.

Tumor cell density was monitored as described in Example 1. The cell death and therefore the reduction of cell density induced by doxorubicin treatment were dependent on the initial drug concentration. For example, the cell density in the periphery of the PC3 xenograft tumor (i.e., about 75 µm thick) decreased with time after treatment with 5 or 20 µM doxorubicin, but not after treatment with 1 µM doxorubicin. FIG. 5 shows the inverse correlation of the average drug concentration in the PC3 xenograft tumor and the tumor cell density in the periphery of the tumor, after treatment with 20 µM doxorubicin.

Summary

In summary, this example shows that (a) the penetration of doxorubicin in tumors is more rapid but the accumulation is lower as the density of epithelial tumor cells decreases, (b) drug-induced apoptosis enhances drug penetration into the inner cell layers of solid tumors, (c) the concentration-dependent drug penetration rate is related to the concentration-dependent apoptotic effect, and (d) the time-dependent drug penetration is related to the kinetics of apoptosis. These findings are qualitatively identical to the findings for paclitaxel (described in Example 1), and indicate apoptosis-inducing pretreatment as a generally applicable principle for enhancing drug penetration into multilayer tissues.

Example 4

Apoptosis-Inducing Pretreatment Enhances Penetration of Large Particles in Multilayer Tissues Two studies were performed to evaluate the ability of apoptosis-inducing pretreatment to enhance the penetration of large molecules in multilayer tissues. The first study used fluorescence-tagged (i.e., FITC-labeled) nanoparticles, which are between 600–800 nm in diameter. The penetration of the nanoparticles was monitored by fluorescence microscopy. The second study used microparticles (about 5 micron in diameter). The penetration of the microparticles was monitored by scanning electron microscopy.

The multilayer tissue model for both studies was the human breast xenograft tumor derived from subcutaneous implantation of MCF7 cells. Tumors were removed from mice, fragmented and grown as histocultures on collagen gel matrix. One group received a pretreatment with 100 nM paclitaxel for 24 hr. The histocultures were then moved to a second culture flask, and incubated in paclitaxel-free culture medium with FITC-nanoparticles or microparticles for additional 48 hr. The control group was treated similarly, except no paclitaxel was added to the culture medium. Samples of histocultures were removed at 0, 4, 6, 12, 24 and 48 hr after exposure to nanoparticles or microparticles. Histocultures were frozen, cut into 10 micron sections. The frozen sections were mounted on microscopic slides and examined microscopically.

The results show that in the control groups, penetration of nanoparticles and microparticles in tumor histocultures in the 48 hour exposure period was limited to the periphery. In the pretreated groups, nanoparticles and microparticles penetrated the center of the histocultures by 24 hr and became evenly distributed throughout the histocultures by 48 hr.

Summary

In summary, apoptosis-inducing pretreatment enhances penetration of particles of about 5 micron diameter in multilayer tissues.

Example 5

Nanoparticle and Microparticle Formulations

Poly(lactide-co-glycolide) (PLGA) microspheres were prepared by a standard oil-in-water emulsion-solvent evaporation method (Thies C., 1991, In Donbrow M. (Ed.) *Microcapsules and Nanoparticles in Medicine and Pharmacy*, CRC Press, Ann Arbor, pp. 47–71). For doxorubicin-containing microspheres, doxorubicin in its free base form, and PLGA were dissolved in a 1:6 mixture of methanol in methylene chloride. Polymer and drug solutions were emulsified in an aqueous solution containing 1% (w/v) polyvinylalcohol and 10 mM boric acid, pH 8.8 by brief vortexing. Subsequently, the emulsion was diluted, and the organic solvents allowed to evaporate. The microspheres were harvested by filtration, and lyophilized. For paclitaxel microspheres, PLGA and paclitaxel were dissolved in methylene chloride. The solution was emulsified with a glycerin/water mixture containing Tween 80. The microspheres were harvested by centrifugation and lyophilized. The average particle size was 1 µm.

Nanoparticles containing paclitaxel were prepared by the phase separation methods. An aqueous solution of gelatin and Tween 20 was heated and sodium sulfate added until turbidity was observed. Paclitaxel-containing isopropanol solution was then added until the turbidity disappeared. Glutaraldehyde and potassium meta-bisulfite were added in sequence. The resulting nanoparticles were harvested by centrifugation and lyophilized. The average particle size was 620 nm.

Nanocapsules containing paclitaxel were prepared by the oil-in-water-in-oil method. Tween 20 was added to 10 acres solution of gelatin. Paclitaxel was dissolved in methylene chloride. The two solutions were emulsified to form an oil-in-water emulsion. Mineral oil containing glutaraldehyde was then added. After teaching the mixture, potassium meta-bisulfite was added. The resulting microparticles were harvested by centrifugation and lyophilized. The average particle size was 13 µm.

Liposomes containing paclitaxel were prepared by mixing triasterin, paclitaxel and Tween 80. Phosphate buffered saline was added while vortexing, to form an emulsion. The lipospheres were harvested by centrifugation. Addition of egg phosphatidylcholine to the mixture improves the smoothness of the particle surface. The average particle size was 10 µm.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

We claim:

1. A method for delivering a therapeutic agent to a tumor in a patient, which comprises the steps of:
    (a) administering a dose of an apoptosis inducing agent paclitaxel to a patient having a tumor;

(b) allowing a time ranging from between about 24 and about 96 hours to elapse for said apoptosis inducing agent to induce greater than about 20% reduced cell density in the tumor; and (c) administering a dose of a therapeutic agent to said patient, such that the therapeutic agent is delivered to the tumor to a greater extent than if administered without said apoptosis inducing agent.

2. The method of claim 1, wherein said therapeutic agent comprises a gene therapy construct, a protein bound drug, a chemotherapeutic agent, or an antibiotic.

3. The method of claim 2, wherein said therapeutic agent is a gene therapy construct, wherein said construct comprises a tumor suppressor gene.

4. The method of claim 3, wherein said tumor suppressor gene is p53.

5. The method of claim 1, wherein said therapeutic agent is a protein bound drug.

6. The method of claim 1, wherein said apoptosis inducing agent is administered systemically.

7. The method of claim 1, wherein said apoptosis inducing agent is administered regionally.

8. The method of claim 1, wherein said apoptosis inducing agent is administered locoregionally.

9. The method of claim 1, wherein said apoptosis inducing agent is administered locally.

10. The method of claim 1, wherein said therapeutic agent is administered systemically.

11. The method of claim 1, wherein said therapeutic agent is administered regionally.

12. The method of claim 1, wherein said therapeutic agent is administered locoregionally.

13. The method of claim 1, wherein said therapeutic agent is administered locally.

14. The method of claim 1, wherein said tumor is cancerous.

15. The method of claim 14, wherein said cancerous tumor is one or more of a brain, breast, ovarian, bladder, prostate, colon, lung, liver, pancreatic, gastric, bile duct, or uterine tumor.

16. The method of claim 1, wherein a dose of said apoptosis inducing agent is about 50 nM, which is administered over about 1 hour.

17. The method of claim 1, wherein said patient is a human.

18. The method of claim 1, wherein said apoptosis inducing agent is also said therapeutic agent but wherein said therapeutic agent is one or more of a separate dose or a slow-release form of the apoptosis inducing agent.

19. The method of claim 1, wherein said therapeutic agent and said apoptosis inducing agent comprises paclitaxel.

20. The method of claim 1, wherein said therapeutic agent comprises doxorubicin.

21. The method of claim 1, wherein said apoptosis inducing agent is formulated as one or more of microparticles or nanoparticles.

22. The method of claim 1, wherein said therapeutic agent is formulated as one or more of microparticles or nanoparticles.

23. The method of claim 1, wherein one or more of said apoptosis inducing agent or said therapeutic agent is administered with a pharmaceutically acceptable carrier.

* * * * *